United States Patent [19]

Seymour

[11] Patent Number: 5,268,148
[45] Date of Patent: Dec. 7, 1993

[54] SALIVA SAMPLING DEVICE AND SAMPLE ADEQUACY SYSTEM

[75] Inventor: Eugene H. Seymour, Pacific Palisades, Calif.

[73] Assignee: Saliva Diagnostic Systems, Inc., Vancouver, Wash.

[21] Appl. No.: 838,609

[22] Filed: Feb. 19, 1992

Related U.S. Application Data

[63] Continuation-in-part of Ser. No. 775,195, Oct. 11, 1991, and Ser. No. 831,776, Feb. 5, 1992, Pat. No. 5,260,031, which is a continuation-in-part of Ser. No. 722,333, Jun. 25, 1991, abandoned, and Ser. No. 629,278, Dec. 18, 1990, abandoned.

[51] Int. Cl.$^5$ .................. C12M 1/28; G01N 33/487; B65D 81/24
[52] U.S. Cl. .................. 422/101; 128/760; 422/58; 422/99; 422/100; 422/102; 435/294; 435/295
[58] Field of Search ............... 128/732, 760, 762, 769; 422/58, 99–102; 435/294–295

[56] References Cited

U.S. PATENT DOCUMENTS

| | | | |
|---|---|---|---|
| 3,449,081 | 6/1969 | Hughes | 422/101 X |
| 3,783,104 | 1/1974 | Henshilwood et al. | 435/295 |
| 3,832,141 | 8/1974 | Haldopoulos | 422/101 |
| 3,966,558 | 6/1976 | Calva-Pellicer | 435/295 |
| 4,014,322 | 3/1977 | Shah | 128/760 |
| 4,209,488 | 6/1980 | Breno | 422/101 |
| 4,268,270 | 5/1981 | Gabbay et al. | 422/58 X |
| 4,312,950 | 1/1982 | Snyder et al. | 435/295 |
| 4,387,725 | 6/1983 | Mull | 435/295 X |
| 4,418,702 | 12/1983 | Brown et al. | 422/102 X |
| 4,444,193 | 4/1984 | Fogt et al. | 422/58 X |
| 4,624,929 | 11/1986 | Ullman | 422/100 X |
| 4,635,488 | 1/1987 | Kremer | 422/58 X |
| 4,770,853 | 9/1988 | Bernstein | 422/58 |
| 4,791,060 | 12/1988 | Chandler | 422/100 X |
| 4,833,087 | 5/1989 | Hinckley | 422/58 X |
| 4,859,603 | 8/1989 | Dole et al. | 422/101 X |
| 4,865,813 | 9/1989 | Leon | 422/101 |
| 4,895,808 | 1/1990 | Romer | 422/101 X |
| 4,961,432 | 10/1990 | Guirguis | 128/760 |
| 5,000,193 | 3/1991 | Heelis et al. | 128/760 |
| 5,079,142 | 1/1992 | Coleman et al. | 422/58 X |
| 5,084,245 | 1/1992 | Berke et al. | 422/101 X |
| 5,100,261 | 3/1992 | Berke et al. | 422/58 X |
| 5,103,836 | 4/1992 | Goldstein et al. | 128/760 |
| 5,135,873 | 8/1992 | Patel et al. | 422/58 X |

FOREIGN PATENT DOCUMENTS 63-293440 11/1988 Japan .................. 128/760

*Primary Examiner*—James C. Housel
*Assistant Examiner*—Arlen Soderquist
*Attorney, Agent, or Firm*—W. Edward Johansen

[57] ABSTRACT

A saliva sampling device includes a collection container, a saliva collector and a sample container. The sample container is inserted into the collection container and becomes fluidly coupled thereto by inserting the saliva collector into sample container and pressing it therein. This allows a sample of saliva to be collected, separated from the saliva collector and retained within the collection container for testing. The saliva collector includes a piston fitting closely within the sample container and a porous mass which may be compressed by the piston in the sample container to extract the sample of saliva for distribution to the collection container. A buffering solution may be retained within the sample container for mixing with the sample of saliva. The saliva sampling device may include a sample container, a saliva collector and at least one reagent container which may be used with a rotatable cylinder to mix a buffered sample of saliva with at least one reagent solution for conducting a laboratory test on site. The saliva sampling device may also include at least two sample containers and at least two saliva collectors which may be used with a cylinder to mix a buffered sample of saliva with at least one reagent solution for conducting a laboratory test on site. This allows at least two people to be tested with the same saliva sampling device.

11 Claims, 14 Drawing Sheets

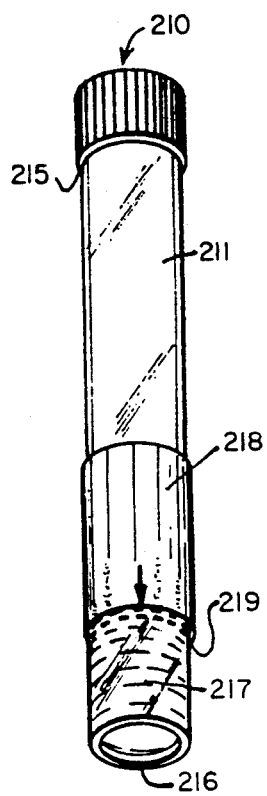
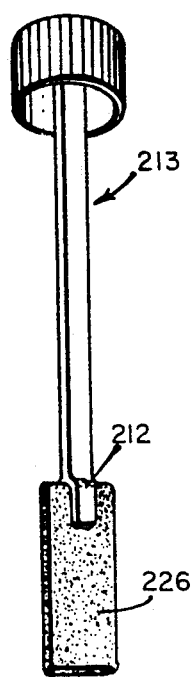
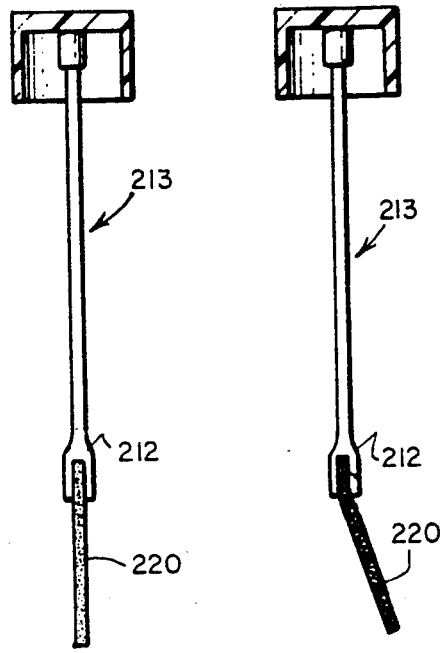
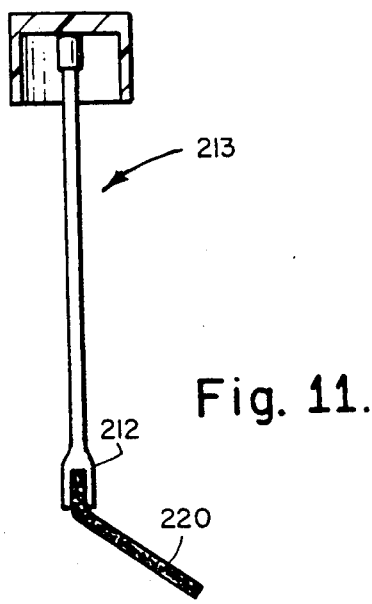
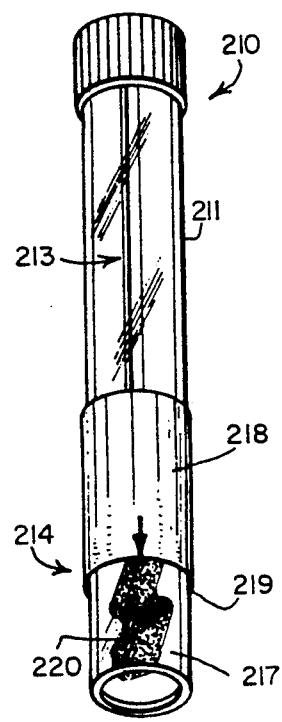
Fig. 7. Fig. 8. Fig. 9. Fig. 10. Fig. 11. Fig. 12.

Fig. 23.
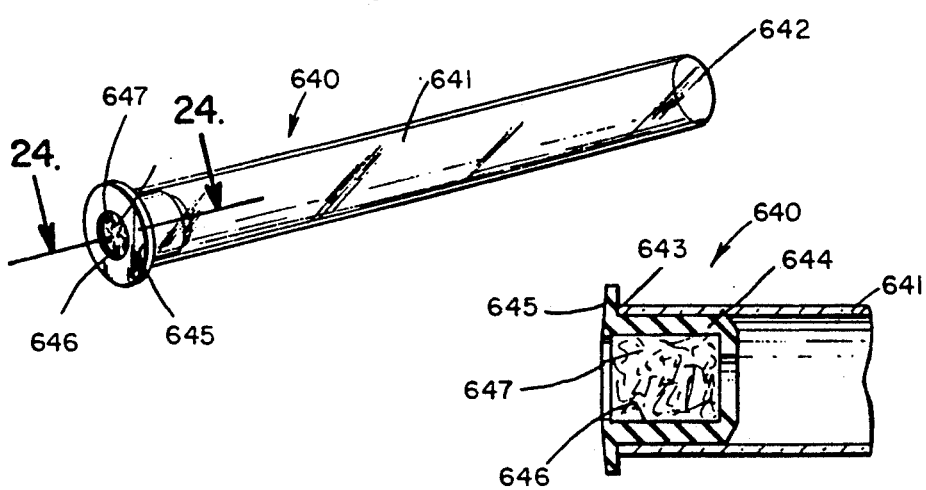
Fig. 24.
Fig. 25.
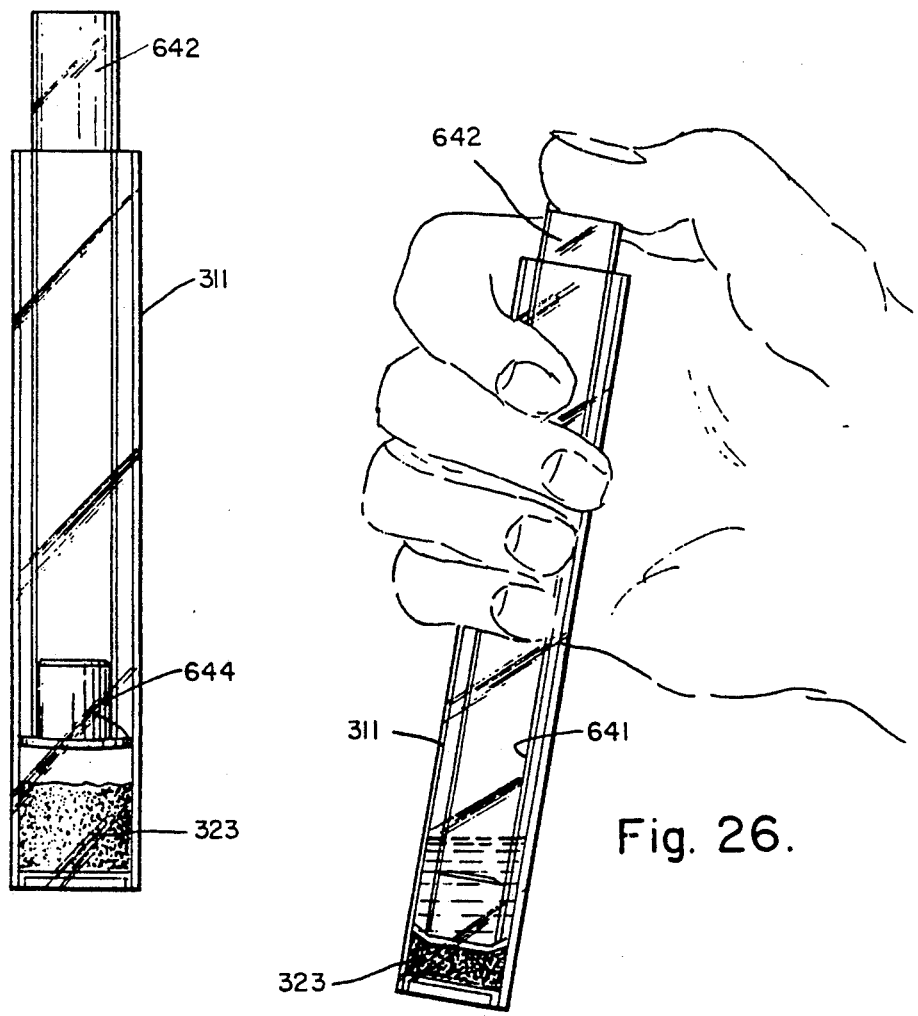
Fig. 26.

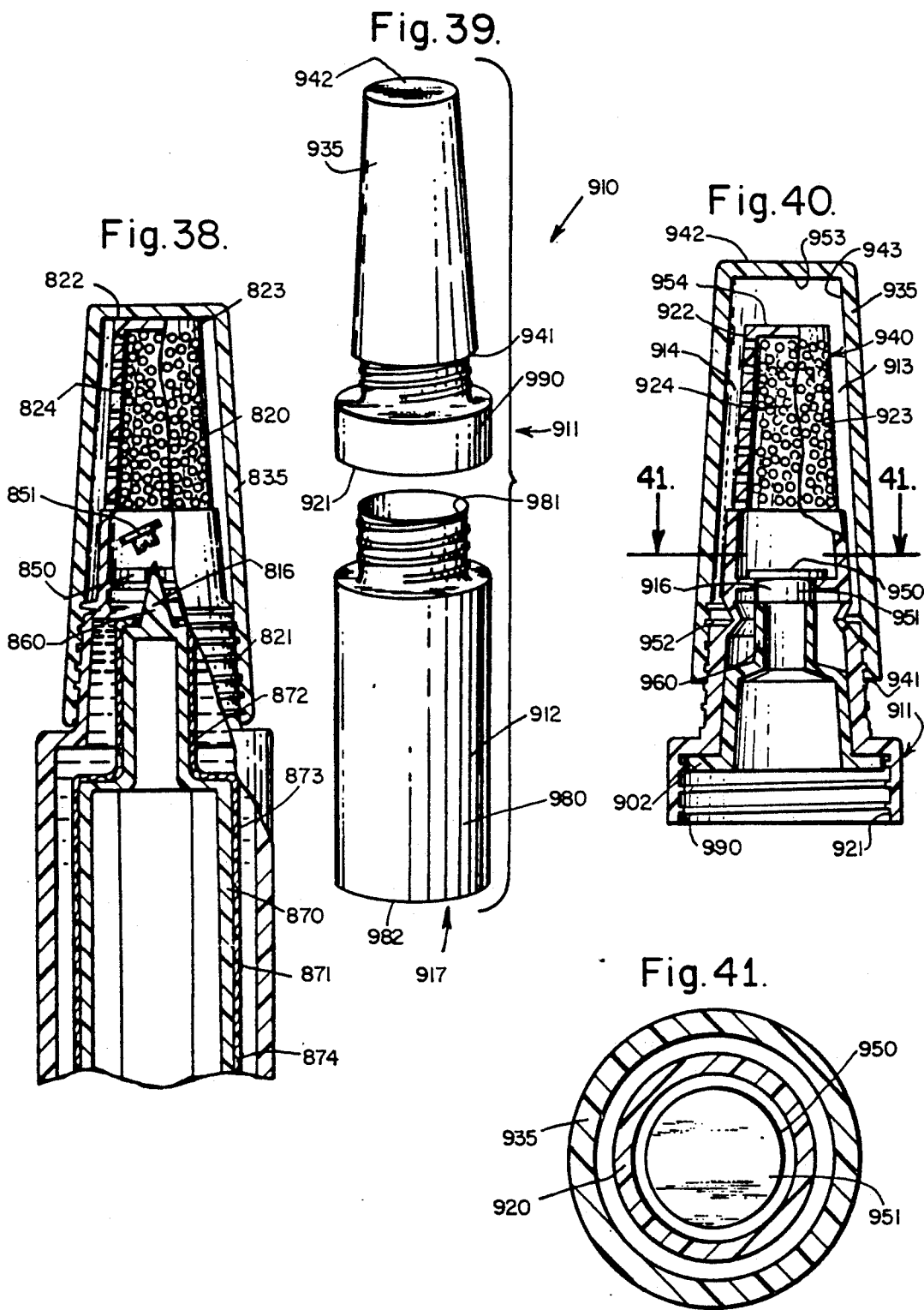

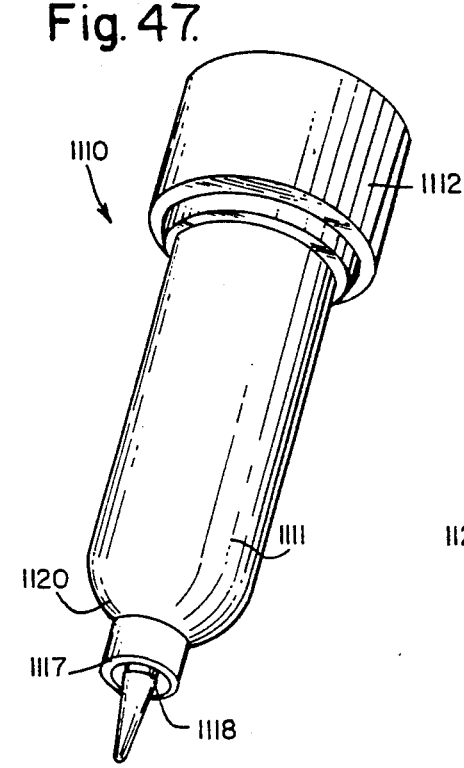
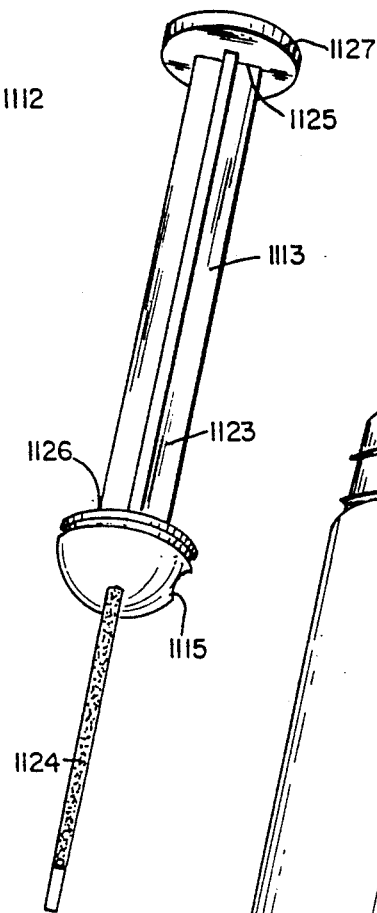
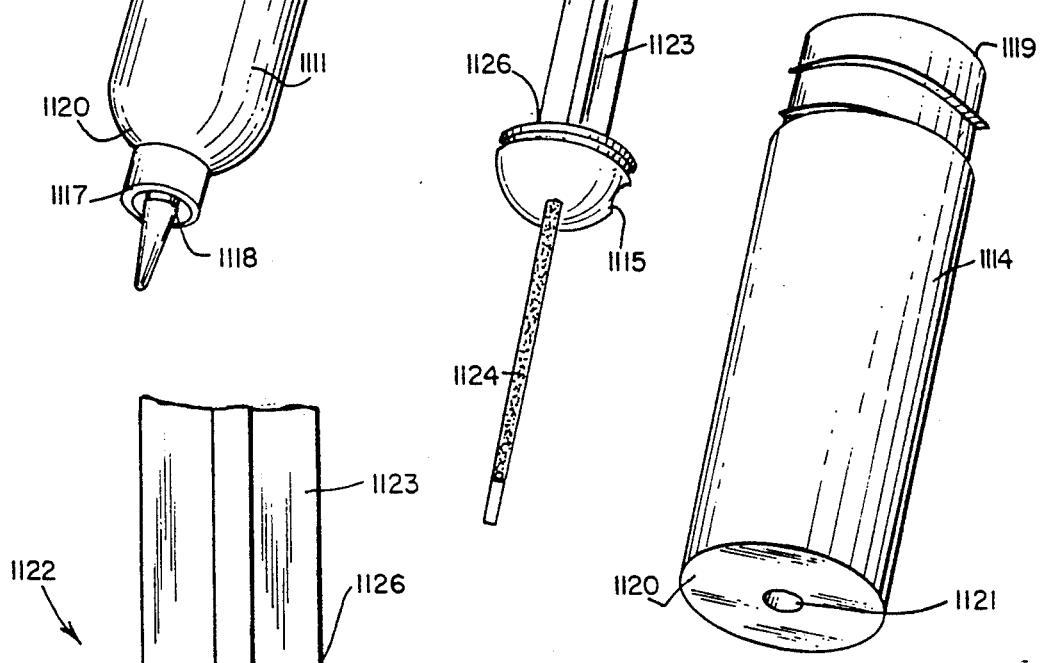
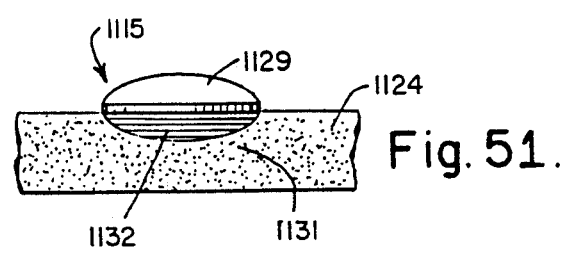
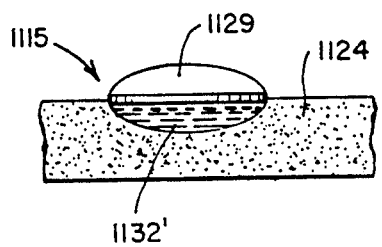
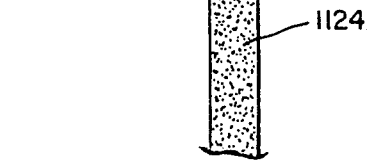

Fig. 53.
Fig. 56.
Fig. 54.
Fig. 55.
Fig. 57.
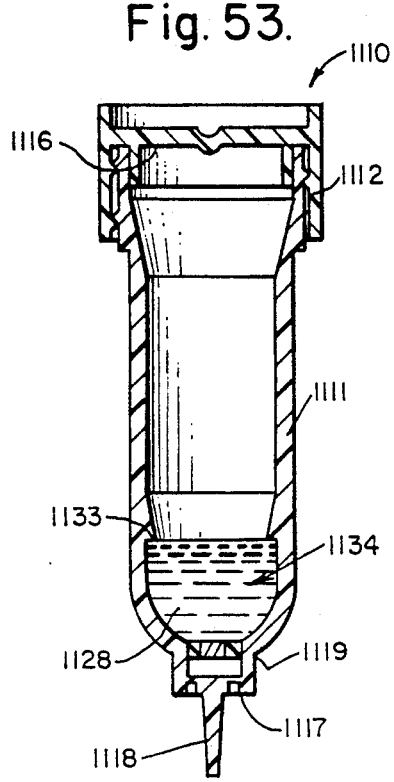
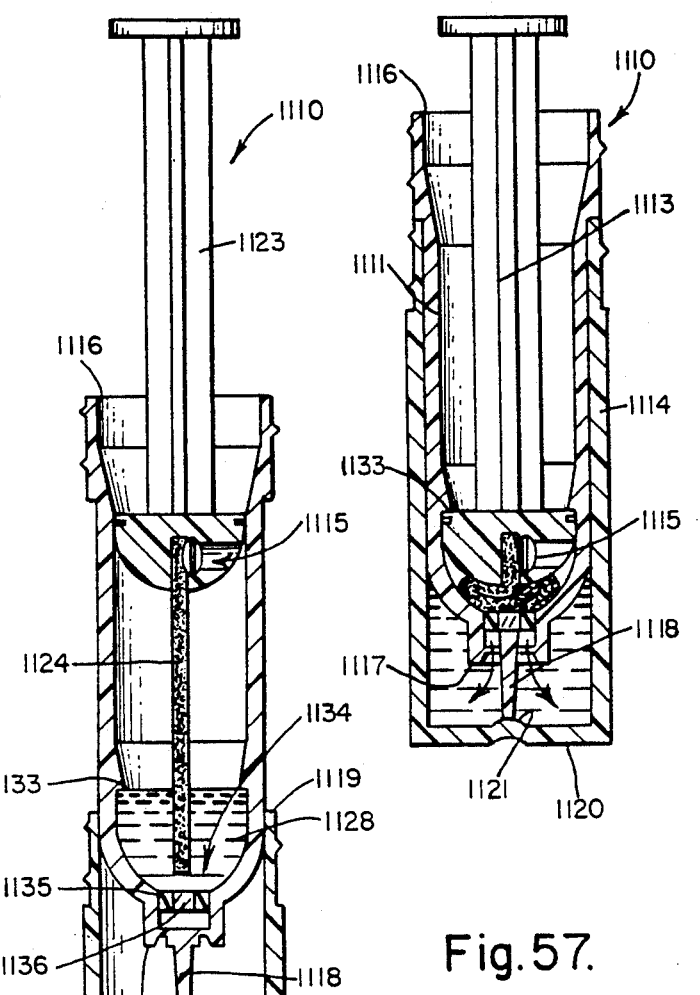
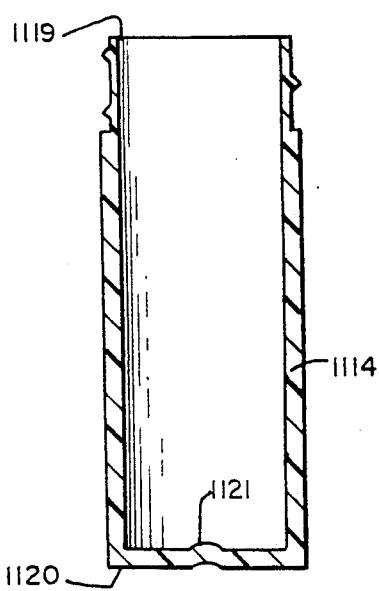
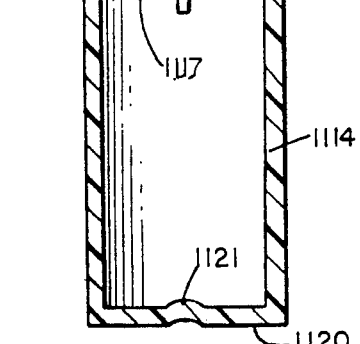
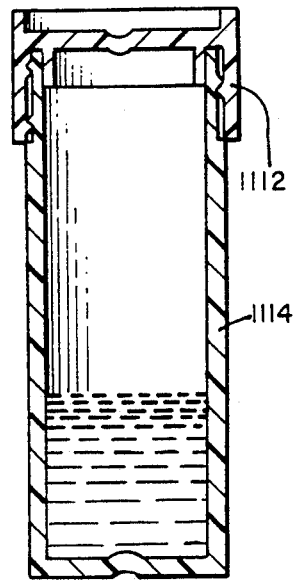

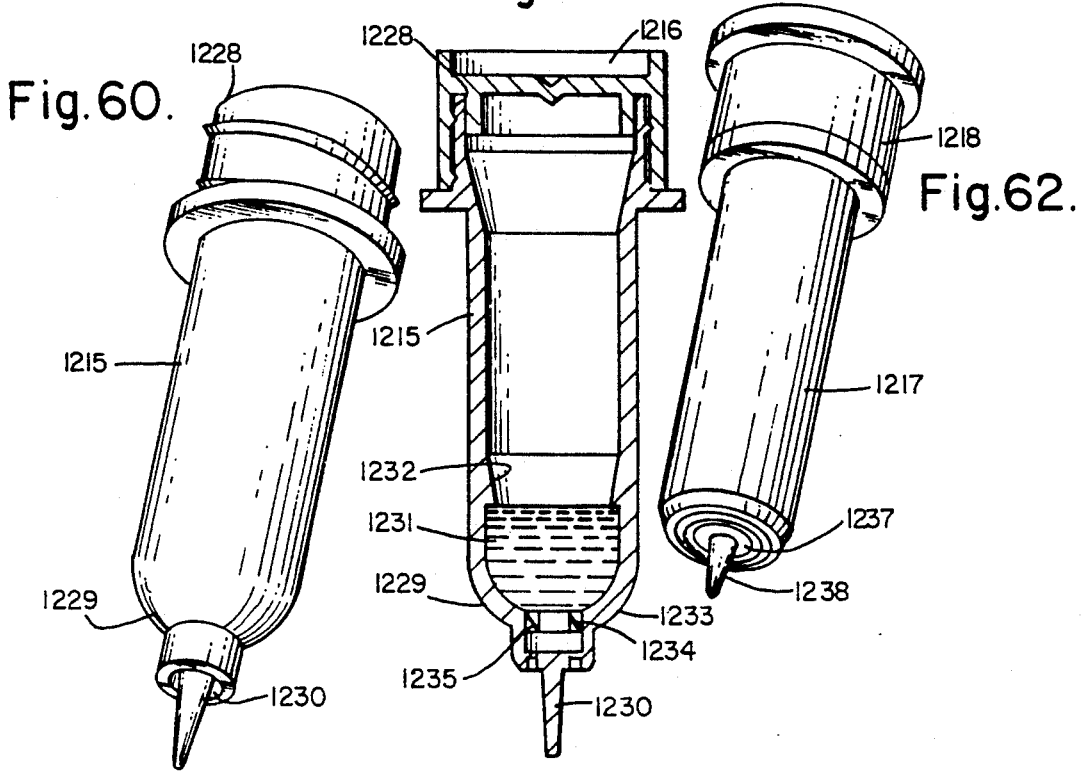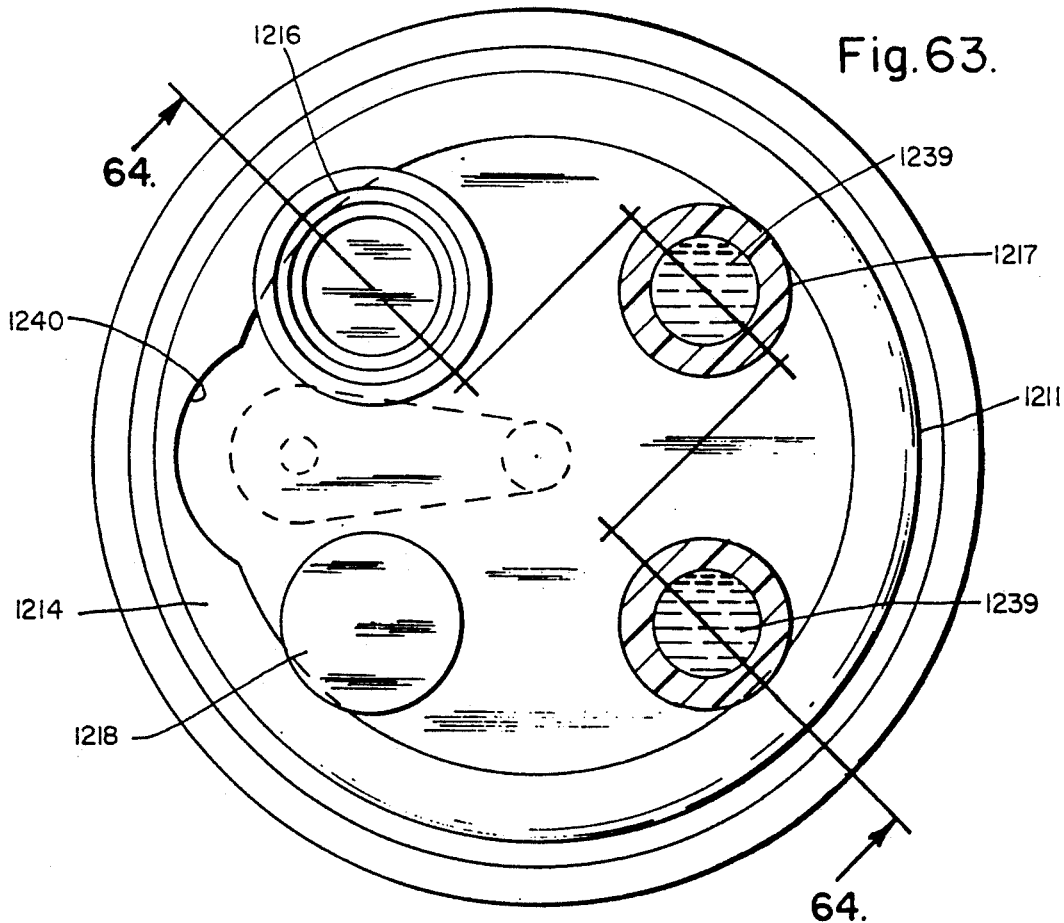

SALIVA SAMPLING DEVICE AND SAMPLE ADEQUACY SYSTEM

This application is a continuation-in-part of both the application filed Feb. 5, 1992 under Ser. No. 07/831,776, now U.S. Pat. No. 5,260,031, and the application filed Oct. 11, 1991 under Ser. No. 07/775,195; the application filed Feb. 5, 1992 under Ser. No. 07/831,776 is a continuation-in-part of both the application filed Jun. 25, 1991 under Ser. No. 07/722,333, now abandoned, and the application filed Dec. 18, 1990 under Ser. No. 07/629,278, now abandoned, the disclosures of which are incorporated herein by reference.

BACKGROUND OF THE INVENTION

1. Field of the Invention

The field of the invention is saliva sampling devices.

2. Description of the Prior Art

The current literature indicates saliva is used to conveniently, easily, safely and effectively test an individual for a variety of medical conditions. These tests for medical conditions include a hepatitis screening for restaurant employees, HIV, continue (nicotine) and cocaine screening by insurance companies and a five minute HIV screening by a dentist. Clinics for oncology, neurology, infertility, allergy orthopedic and pain which had used urine, blood and serum samples to determine the medical conditions of their patients are now using samples of saliva for this same purpose.

U.S. Pat. No. 5,079,170 teaches a sample applicator for use in performing immunoassays which includes a tube which defines an internal lumen and has a filter matrix at one end thereof. The sample is drawn into the applicator tube. The applicator may also include a reagent which is dispersed within a permeable matrix.

U.S. Pat. No. 5,077,198 teaches that diluent and wash compositions are useful in a rapid and sensitive assay for detecting antibodies, and especially retroviral antibodies, in a biological specimen. The diluent composition is buffered to a Ph of 6 to 10 and includes a protein or carbohydrate, a surfactant and a negatively-charged organic compound. The wash composition is buffered to a Ph of 5 to 10 and includes a surfactant. These compositions can be included in a diagnostic kit. The method includes mixing the biological specimen with the diluent composition, forming an immunological complex between ligand and antibodies in the specimen and separating complexed materials from uncomplexed materials using a filtration membrane and a washing step. An enzyme labeled anti-antibody is added to form a ligand-antibody-antibody complex followed by its detection using suitable reagents.

U.S. Pat. No. 4,834,110 teaches a selective collector of a human patient's saliva for monitoring or analysis is formed as a substantially conical flat concave cup of resilient molded polymer with tubing connections at an apex portal, and a large entrance portal having a soft compliant foam elastomer rim positioned for contact with the patient's soft tissue, such as the interior of the patient's cheek around the parotid salivary duct. Suction is connected to the soft foam rim, holding the concave cup in position, and suction, fixed pressure, pulsing pressure or electrical stimulation may promote the flow of saliva to a collector vessel. U.S. Pat. No. 4,768,238 teaches a bifurcated vessel for the collection of saliva.

U.S. Pat. No. 4,150,950 teaches a sampling device which includes a container, a seal, a screw-cap, an elongated element and a specimen collector. The container has a liquid reagent which the seal seals into the bottom portion thereof capable of preserving the activity of a particular specimen. The specimen collector is attachable to the inside of the screw cap through the elongated element which is of sufficient length to immerse the specimen collector into the liquid. After a specimen has been obtained, the specimen collector, which is attached to the screw cap, is forced through the seal into the liquid preservative as the screw cap is fastened tightly onto the container.

U.S. Pat. No. 4,774,962 teaches a method of extracting human saliva in which a resilient absorbent inert body is chewed by a person and is subsequently introduced into a centrifuge tubule provided with an apertured floor. The centrifuge tubule is introduced into a centrifuge and subjected to a spinning process, whereupon the saliva is pressed out of the resilient body and passes through the floor into the lower part of the centrifuge tubule.

U.S. Pat. No. 4,992,296 teaches a drug abuse test paper which are bibulous paper carriers which have been impregnated with specific test chemicals, including bismuth nitrate, potassium iodide, acetic acid, and platinum salt, in two coatings and dried after each coating under specific temperature conditions. The test chemicals are provided for the detection of the drug abuse compounds of amphetamine, cocaine, marijuana, and narcotics contained in low concentrations in animal or human urine.

U.S. Pat. No. 4,635,488 teaches a body fluid sampling device which includes a hollow tube with a solid, porous, water-wetable non-fibrous nib mounted in and protrudes from one end of the tube for collecting, by absorption, a sample of a body fluid such as sweat, tears, or saliva. The sample may be extracted from the nib for analysis by supplying an extraction fluid to the interior of the tube for gravity. Alternatively, a strip of paper, which contains an agent that changes appearance to indicate the presence of a substance to be detected, may be disposed in the hollow tube for endwise contact with the nib to receive the sample or components thereof by absorption.

U.S. Pat. No. 4,580,577 teaches a method for collecting saliva from a test subject which includes providing a flavored absorbent sponge for mastication and charging it with saliva and then expressing the saliva from the flavored absorbent sponge. The apparatus for this method includes a barrel-piston arrangement in association with a specimen vial for storage until diagnostic testing.

U.S. Pat. No. 4,817,632 teaches an oral fluid collection article for placement in the buccal cavity of an individual for the collection and filtering of a saliva fluid. The collection article has a semi-permeable membrane container enclosing an osmotic membrane.

U.S. Pat. No. 4,607,009 teaches an assay for determining the Lewis blood group of a patient which consists of testing a body sample for the presence of Lewis antigens. Mono-clonal antibodies specific for either of these antigens are employed which do not cross-react with other related antigens. Body samples which may be tested include saliva, serum, urine, and paraffin-embedded tissue samples.

U.S. Pat. No. 4,720,455 teaches a test kit of several reagents, test tubes and a dip-stick carrying an anti-progesterone mono-clonal antibody. U.S. Pat. No.

4,722,889 teaches a reagent kit is provided for assay of a selected antigen in an aliquot of body fluid.

U.S. Pat. No. 4,769,216 teaches a test kit which is used in detecting or determining the presence of antigenic or haptenic substances or antibodies in a sample. The test kit includes a plurality of tubular or capillary elements, each having antibodies or antigenic or haptenic substances attached to an internal surface thereof, and mechanism for causing fluids to pass simultaneously or sequentially through the plurality of capillary elements.

U.S. Pat. No. 4,771,486 teaches a sputum-saliva sampling device having capability for sputum-saliva separation which includes a substantially circular cup having a wall portion which tapers inwardly from top to bottom, a separation plate having a substantially elliptical planar configuration, the major and minor axis of the plate being dimensioned to allow insertion of the plate down into the cup at a slant to position the lower portion of the plate a distance above the bottom of the cup, a plurality of apertures formed in the lower portion of the plate to provide saliva drainage ports, and an upper portion of the plate comprising a roughened textured surface for retracting and holding sputum in position for recovery in order to obtain a sensory and microbiological examination.

U.S. Pat. No. 4,853,325 teaches a saliva test for feline leukemia virus (FeLV) which includes a probe which has an immuno-chemically sensitive member for collecting saliva from the oral cavity of a cat. The probe employs ELISA reagents for the incubation of the probe and the development of color reactions to indicate the presence or absence of FeLV within the saliva sample collected onto the probe.

U.S. Pat. No. 4,468,470 teaches a method for the assay of antibodies to soluble antigens in an aqueous sample in body fluids, such as blood serum or blood plasma, by contacting the sample with an antigen in vitro. The antibodies, if present, are bound by the antigens.

U.S. Pat. No. 4,929,544 teaches that human cancer is diagnosed/monitored by measuring an antigen level in a physiological fluid specimen of a subject by a quantitative immunoassay. That antigen level is then compared to the antigen level of that occurs in corresponding physiological fluid of normal subjects to determine whether the former is substantially elevated over the latter.

U.S. Pat. No. 4,942,122 teaches a kit which detects the presence of an antibody inhibiting HIV reverse transcriptase. The amount of antibody inhibiting HIV reverse transcriptase present in the body fluids of a patient known to be immuno-positive for HIV gives the clinician a means to form a prognosis for each individual case.

U.S. Pat. No. 4,447,528 teaches a radio-assay reagent kit for detecting auto blocking antibody. A receptor is immobilized on a support and the amount of ligand capable of binding therewith in the presence of a biological fluid sample is determined.

U.S. Pat. No. 4,865,966 teaches a method of screening mammals for antibodies to viral agents in which a urine sample is collected from a mammal to be tested. The urine sample is assayed the sample for antibodies directed against the specific viral agent.

SUMMARY OF INVENTION

The present invention is directed to a saliva sampling device includes a collection container, a saliva collector and a sample container wherein the sample container can be inserted into the collection container and can be fluidly coupled thereto. With such a device a sample of saliva may be collected, separated from the saliva collector and retained within the collection container for testing.

In another aspect of the present invention the saliva collector includes a piston fitting closely within the sample container and a porous mass which may be compressed by the piston in the sample container to extract the sample of saliva for distribution to the collection container. A buffering solution may be retained within the sample container for mixing with the sample of saliva.

Other aspects and many of the attendant advantages will be more readily appreciated as the same becomes better understood by reference to the following detailed description and considered in connection with the accompanying drawing in which like reference symbols designate like parts throughout the figures.

The features of the present invention which are believed to be novel are set forth with particularity in the appended claims.

DESCRIPTION OF THE DRAWING

FIG. 7 is a perspective view of a sample container of a saliva sampling device in accordance with the principles of the third embodiment.

FIG. 8 is a perspective view of a saliva collector including a holder, a elongated member and a piece of filter paper in accordance with the principles of the third embodiment.

FIG. 9 is a side elevational view in cross-section of the saliva collector of FIG. 8 before the saliva collector has been placed in a subject's mouth.

FIG. 10 is a side elevational view in cross-section of the saliva collector of FIG. 8 after the saliva collector has been placed in a subject's mouth, but before it has collected an adequate sample of saliva.

FIG. 11 is a side elevational view in cross-section of the saliva collector of FIG. 8 after the saliva collector has collected an adequate sample of saliva.

FIG. 12 is a perspective view of the sample container of FIG. 7 and the saliva collector of FIG. 8 after the saliva collector has collected an adequate sample of saliva.

FIG. 23 is a perspective view of a hollow piston which includes a first open end, a second open end and a cylindrical, rubber gasket which is snugly disposed in the second end and which is slidably coupled to the sample container of FIG. 13.

FIG. 24 is partial longitudinal view in cross-section of the hollow piston of FIG. 23 the cylindrical, rubber gasket of which has a flange and an opening into which a filter is placed for use in separating the measured sample of a saliva from the piece of filter paper.

FIG. 25 is a side elevational view of the saliva sampling device of FIG. 13 and the hollow piston of FIG. 23.

FIG. 26 is a schematic drawing showing the sample container of FIG. 13 and the hollow piston of FIG. 23 being used to press the saliva from the sample container into hollow piston.

FIG. 38 is a longitudinal view in cross-section of saliva sampling device of FIG. 34.

FIG. 39 is a perspective view of a saliva sampling device in accordance with the principles of the tenth embodiment.

FIG. 40 is a partial longitudinal view in cross-section of the saliva sampling device of FIG. 39.

FIG. 41 is a transverse view in cross-section of the saliva sampling device of FIG. 40 taken along line 41—41 of FIG. 40.

FIG. 47 is a perspective view of a sample container of a saliva sampling device in accordance with the principles of the twelfth embodiment.

FIG. 48 is a perspective view of a saliva collector of the saliva sampling device of FIG. 47 which includes a holder, an elongated member, a piece of filter paper and a sample adequacy system.

FIG. 49 is a perspective view of a collection container of the saliva sampling device of FIG. 47.

FIG. 50 is an elevational view in a partial cross-section of the sample adequacy system of the saliva collector of FIG. 48.

FIG. 51 is a cross-sectional view of the saliva collector of FIG. 48 taken along line 51—51 of FIG. 50 showing the sample adequacy system before the saliva collector has been placed in a subject's mouth.

FIG. 52 is a cross-sectional view of the saliva collector of FIG. 48 taken along line 51—51 of FIG. 50 showing the sample adequacy system after the saliva collector has collected an adequate sample of saliva.

FIG. 53 is an elevational view in cross-section of the sample container of FIG. 47 with the sample container including a breakable seal and containing a buffering solution.

FIG. 54 is an elevational view in cross-section of the collection container of FIG. 49.

FIG. 55 is an elevational view in cross-section of the sample container of FIG. 47 after the cap has been removed from the the sample container, the sample container has been placed in the collectoin container of FIG. 49 and the saliva collector of FIG. 48, which has collected an adequate sample of saliva, has been inserted into the sample container, but before the saliva collector has been pressed downward, so that the sample of saliva is mixed with the buffering solution.

FIG. 56 is an elevational view in cross-section of the sample container of FIG. 47 after the saliva collector of FIG. 48 has been pressed downward into the collection container of FIG. 49 to break the breakable seal thereof in order to release the mixture of the buffering solution and the saliva s that this mixture flows into the collection container.

FIG. 57 is an elevational view in cross-section of the collection container of FIG. 49 which has the mixture of the buffering solution and the saliva contained therein and which is sealed by the cap of the sample container of FIG. 47.

FIG. 60 is a perspective view of a sample container of the saliva sampling device of FIG. 58.

FIG. 61 is an elevational view in cross-section of the sample container of FIG. 60 with the sample container including a cap, a breakable seal and containing a buffering solution.

FIG. 62 is a perspective view of one of three reagent containers of the saliva sampling device of FIG. 58 with each of the reagent containers including a cap, a breakable seal and containing one of three pre-selected reagent solutions.

FIG. 63 is a top plan view in partial cross-section of the saliva sampling device of FIG. 58 taken along the line 63—63 of FIG. 64 which has a rotatable cylinder, which has four bores into each of which one of the sample container and the three reagent containers is disposed in a first vertical position and which is in the blocking position, and a retaining ring which retains each of the sample container and the three reagent containers in their first vertical position with the retaining ring having a release notch, which is aligned with a seal-breaking mechanism and which may be selectively aligned with each of the four bores by rotating the rotatable cylinder from the blocking position to one of four non-blocking positions showing the saliva sampling device before the cap has been removed from the sample container of FIG. 60.

FIG. 64 is an elevational view in cross-section of the saliva sampling device of FIG. 58 taken along the line 64—64 of FIG. 63 showing the saliva sampling device, including a collection container, after the cap of the sample container of FIG. 60 has been removed and the saliva collector of FIG. 59, which has collected an adequate sample of saliva, has been inserted into the sample container so that the sample of saliva is mixed with the buffering solution, but before the rotatable cylinder of FIG. 63 has been rotated from the blocking position to one of the four non-blocking positions.

FIG. 65 is a top plan view in partial cross-section of the saliva sampling device of FIG. 58 taken along the line 65—65 of FIG. 66 showing the saliva sampling device after the rotatable cylinder of FIG. 63 has been rotated from the blocking position to the first non-blocking position.

FIG. 66 is an elevational view in cross-section of the saliva sampling device of FIG. 58 taken along the line 66—66 of FIG. 65 showing the saliva sampling device after the saliva collector has been pressed downward, so that the sample of saliva is mixed with the buffering solution.

FIG. 67 is a cross-sectional view of the saliva sampling device of FIG. 58 taken along the line 67—67 of FIG. 66 showing the seal-breaking mechanism of FIG. 63.

FIG. 68 is a cross-sectional view of the saliva sampling device of FIG. 58 taken along the line 68—68 of FIG. 66 showing the collection container of FIG. 64.

FIG. 69 is a partial cross-sectional view of a locking mechanism of the saliva sampling device of FIG. 58 taken along the line 69—69 of FIG. 66.

FIG. 70 is a top plan view in partial cross-section of the saliva sampling device of FIG. 58 taken along the line 70—70 of FIG. 71 showing the saliva after the rotatable cylinder of FIG. 63 has been rotated from the first non-blocking position to the second non-blocking position.

FIG. 71 is a partial elevational view in cross-section of the saliva sampling device of FIG. 58 taken along the line 71—71 of FIG. 70 showing the saliva sampling device before the reagent container has been pressed downward.

FIG. 72 is a partial elevational view in cross-section of the saliva sampling device of FIG. 58 taken along the line 71—71 of FIG. 70 showing the saliva sampling device after the first reagent container of FIG. 62 has been pressed downward to break the breakable seal of the first reagent container so that the mixture of the buffering solution and the saliva has been mixed with the first preselected reagent solution.

FIG. 73 is a perspective view of a saliva sampling device in accordance with the principles of the fourteenth embodiment.

FIG. 74 is an elevational view of one of five saliva collector of the saliva sampling device of FIG. 73 each of which includes a holder, an elongated member, a piece of filter paper and a sample adequacy system.

FIG. 75 is a top plan view in partial cross-section of the saliva sampling device of FIG. 73 taken along the line 75—75 of FIG. 76 which has a cylinder, which has five bores into each of which one of five sample containers is disposed in a first vertical position and each of which is aligned with one of five seal-breaking mechanisms.

FIG. 76 is an elevational view in cross-section of the saliva sampling device of FIG. 73 taken along the line 76—76 of FIG. 75 showing the saliva sampling device of FIG. 73 including a collection container, after the cap of each of five sample container of FIG. 73 has been removed and each of five saliva collectors of FIG. 74, which has collected an adequate sample of saliva, has been inserted into one of the five bores in the sample container so that the five different samples of saliva, from the different people, are mixed with the buffering solution in each sample container.

FIG. 77 is a cross-sectional view of the saliva sampling device of FIG. 73 taken along the line 77—77 of FIG. 76 showing five seal-breaking mechanisms of FIG. 75.

FIG. 78 is a cross-sectional view of the saliva sampling device of FIG. 73 taken along the line 78—78 of FIG. 76 showing the collection container of FIG. 76.

FIG. 79 is a perspective view of a saliva sampling device in accordance with the principles of the fifteenth embodiment.

FIG. 80 is a front elevational view of a saliva collector of the saliva sampling device of FIG. 79 which includes a holder, an elongated member and a piece of filter paper.

FIG. 81 is a side elevational view of a saliva collector of FIG. 80.

FIG. 82 is a side elevational view of a testing mechanism of the saliva sampling device of FIG. 79.

FIG. 83 is a top plan view of the testing mechanism of FIG. 82.

FIG. 84 is a side elevational view cross-section of the saliva sampling device of FIG. 79.

FIG. 85 is a side elevational view of a collector container of the saliva sampling device of FIG. 79.

FIG. 86 is a side elevational view in cross-section of the collector container of FIG. 85.

FIG. 87 is a side elevational view in cross-section of a saliva sampling device, including an automatic testing mechanism, in accordance with the principles of the sixteenth embodiment.

FIG. 88 is a side elevational view in cross-section of the automatic testing mechanism of FIG. 87.

FIG. 89 is an exploded perspective of the automatic testing mechanism of FIG. 87.

FIG. 90 is an exploded perspective of an automatic testing mechanism in accordance with the principles of the seventeenth embodiment.

DESCRIPTION OF THE PREFERRED EMBODIMENT

Figure 1:
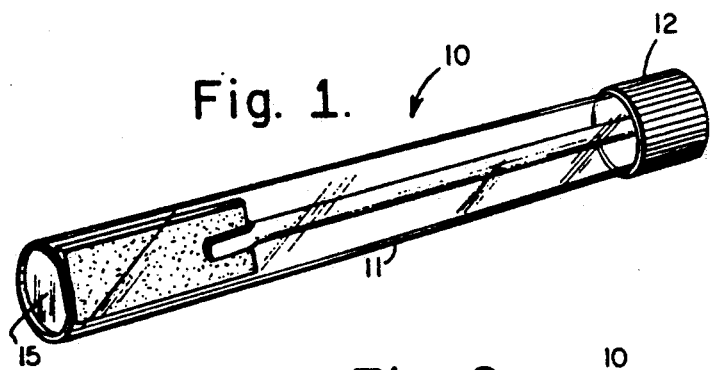
FIG. 1 is a perspective view of a saliva sampling device which includes a sample container and a saliva collector including a holder, an elongated member and a piece of filter paper, a sample adequacy system in accordance with the principles of the first embodiment.
Figure 2:
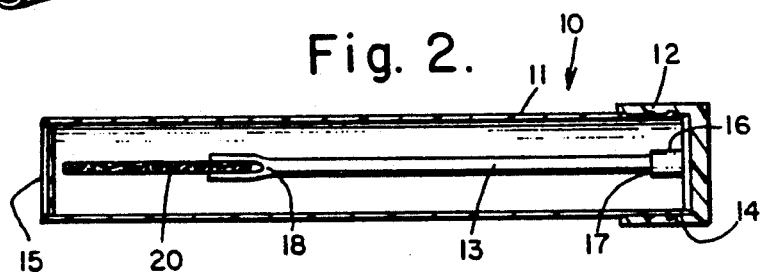
FIG. 2 is a side elevational view in cross-section of the saliva sampling device of FIG. 1.

Referring to FIG. 1 in conjunction with FIG. 2, a saliva sampling device 10 is used for collecting a measured sample of saliva. The saliva sampling device 10 includes a sample container 11, a cap 12 and a saliva collector 13, which is an elongated member. The sample container 11 has an open threaded end 14 and a closed end 15. The cap 12 has an inner surface 16 and is adapted to be mechanically coupled to the open threaded end 14 of the sample container 11 so that the cap 12 seals the sample container 11 air-tight. The saliva collector 13 has a first end 17 and a second end 18 with the first end 17 of which being mechanically coupled to the inner surface 16 of the cap 12. The saliva sampling device 10 also includes a piece of filter paper 20 which is of predetermined dimensions and which is mechanically coupled to the second end 18 of the saliva collector 13, so that a technician can collect a sample of saliva without touching the sample. Each sample of saliva is being collected wet and during the initial stages of testing of the saliva sampling device 10 a corresponding sample of blood serum is being compared thereto.

Figure 3:
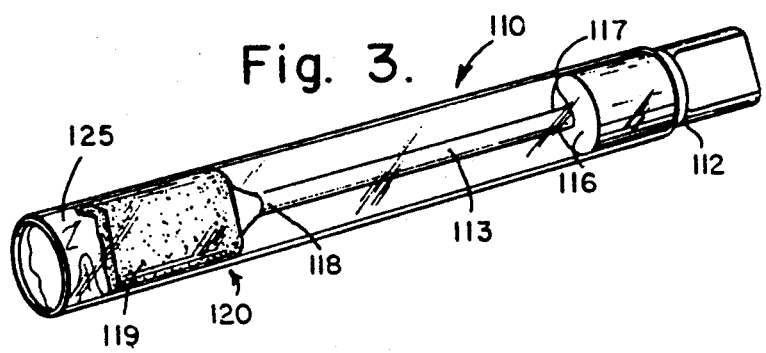
FIG. 3 is a perspective view of a saliva sampling device which includes a sample container and a saliva collector including a holder, a elongated member and a piece of filter paper in accordance with the principles of the second embodiment.
Figure 4:
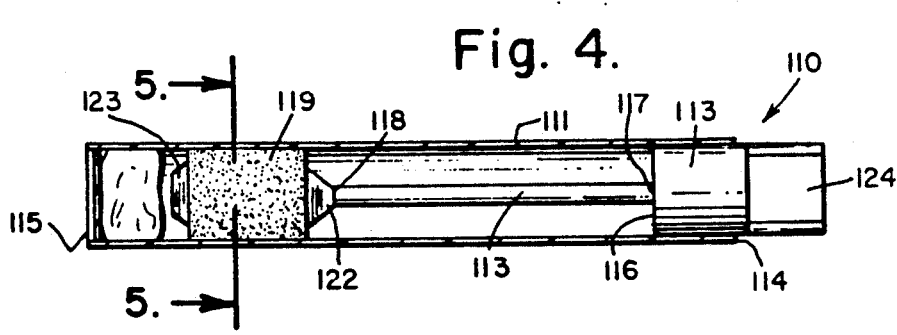
FIG. 4 is a side elevational view in cross-section of the saliva sampling device of FIG. 3.

Referring to FIG. 3 in conjunction with FIG. 4 a saliva sampling device 110 is used for collecting a measured sample of saliva. The saliva sampling device 110 includes a sample container 111, a plug 112 and a saliva collector 113, which is an elongated member. The sample container 111 has an open end 114 and a closed end 115. The plug 112 has an inner surface 116 and is adapted to be slidably coupled to the open end 114 of the sample container 111. The plug 112 seals the container 111 air-tight. The saliva collector 113 has a first end 117 and a second end 118. The first end 117 of the saliva collector 113 is mechanically coupled to the inner surface 116 of the plug 112.

Figure 5:
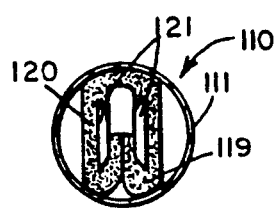
FIG. 5 is an end view in cross-section of the saliva sampling device of FIG. 3 taken along line 5—5 of FIG. 4.
Figure 6:
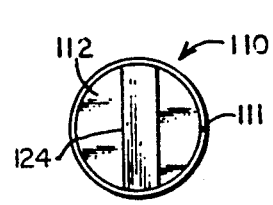
FIG. 6 is a top plan view of the saliva sampling device of FIG. 3.

Referring to FIG. 3 in conjunction with FIG. 4 and FIG. 5 the saliva sampling device 110 also includes a piece of filter paper 119 of pre-determined dimensions and a rectangular paddle assembly 120. The rectangular paddle assembly 120 includes two parallel and contiguous flat plates 121 each of which has a first end 122 and a second end 123 and which are joined together at their first ends 122 and mechanically coupled to the second end 118 of the saliva collector 113. The piece of filter paper 119 is mechanically coupled to the rectangular paddle assembly 120 so that a technician can collect the measured sample of saliva without touching the sample. The saliva sampling device 110 further includes a labeling mechanism 124 and a dessican 125. The labeling mechanism 124 labels the sample container 111 with the name of the patient and the date when the measured sample of saliva was taken. The dessican 125 removes the moisture content from the collected sample of saliva. The saliva sampling device 110 may also include a mailer which is used to transport the collected sample of saliva to a clinical laboratory for processing and analysis.

Referring to FIG. 7 in conjunction with FIG. 8 and FIG. 9 a saliva sampling device 210 includes a sample container 211, a holder 212, a saliva collector 213 and a sample adequacy system 214. The sample container 211 has an open end 215 and a closed end 216. The sample adequacy system includes a solution 217 which is contained in the sample container 211 at a liquid level and a label 218 which has a bottom edge and which is attached to the sample container 211. The bottom edge 219 of the label 218 is disposed adjacent to the liquid level of the solution 217. The saliva collector 213 is a piece of filter paper 220 which is fixed to the holder 212. The saliva collector 213 collects a sample of saliva. The sample adequacy system 214 determines that the collected sample of saliva is an adequate sample when the saliva collector 213 is placed in the sample container 211 and the liquid level of the solution 217 does not drop below the bottom edge 219 of the label 218.

Referring to FIG. 8 in conjunction with FIG. 9 the saliva collector 213 is shown before the saliva collector 213 has been placed in a subject's mouth.

Referring to FIG. 10 the saliva collector 213 is shown after the saliva collector 213 has been placed in a subject's mouth, but before it has collected an adequate sample of saliva.

Referring to FIG. 11 the saliva collector 213 is shown after the saliva collector 213 has collected an adequate sample of saliva.

Referring to FIG. 12 after the saliva collector 213 has collected an adequate sample of saliva, the saliva collector 213 is placed in the sample container 211 if the liquid level of the solution 217 does not drop below the bottom edge 219 of the label 218. If the liquid level of the solution 217 drops below the bottom edge 219 of the label 218 then the sample of saliva is not adequate.

Figure 13:
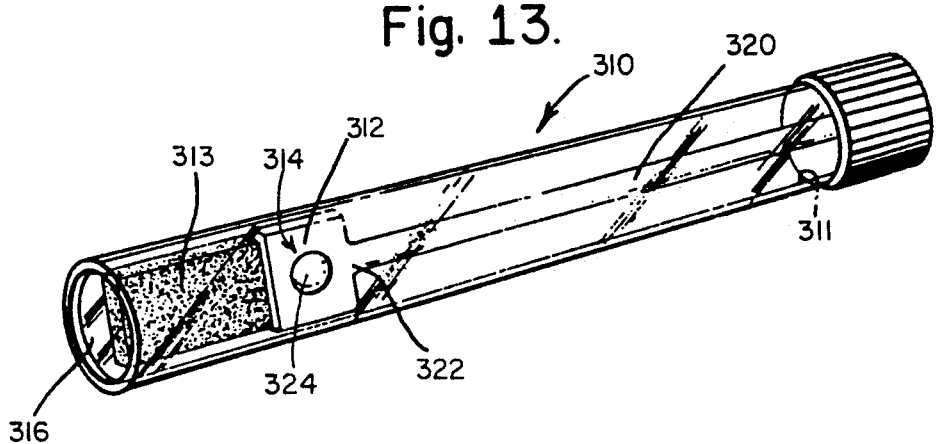
FIG. 13 is a perspective view of a saliva sampling device which includes a sample container, a saliva collector including a holder, a elongated member, a piece of filter paper and a sample adequacy system in accordance with the principles of the fourth embodiment.
Figure 14:
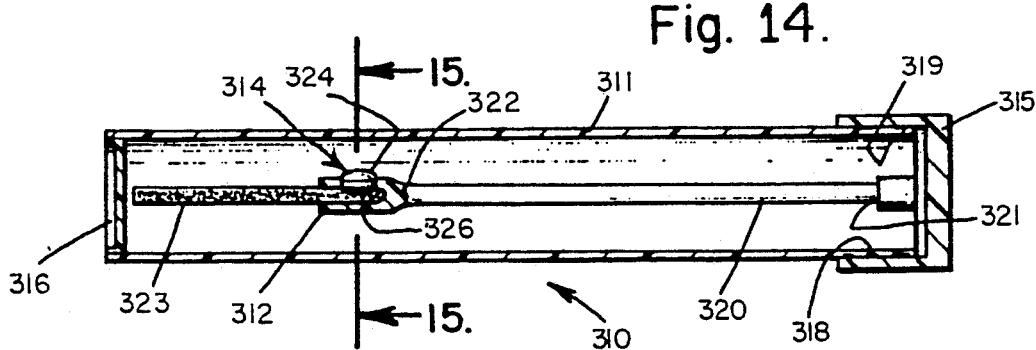
FIG. 14 is a longitudinal view in cross-section of the saliva sampling device of FIG. 13.
Figure 15:
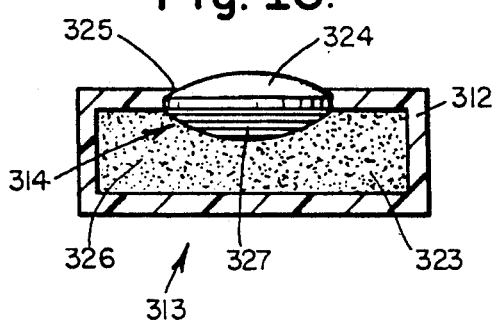
FIG. 15 is a cross-sectional view of the saliva collector of the saliva sampling device of FIG. 13 taken along line 15—15 of FIG. 14 showing the sample adequacy system before the saliva collector has been placed in a subject's mouth.
Figure 16:
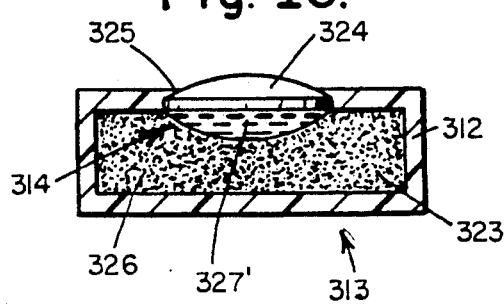
FIG. 16 is a cross-sectional view of the saliva collector of FIG. 13 taken along line 15—15 of FIG. 14 showing the sample adequacy system after the saliva collector has collected an adequate sample of saliva.

Referring to FIG. 13 in conjunction with FIG. 14 a saliva sampling device 310 includes a sample container 311, a holder 312, a saliva collector 313 and a sample adequacy system 314. A solution 317 may be contained in the sample container 311. The sample container 311 has an open threaded end 315 and a closed end 316. A cap 318 has an inner surface 319 and is coupled to the open threaded end 315 of the sample container 311 so that the cap 318 seals the sample cylinder 311 air-tight. An elongated member 320 has a first end 321 and a second end 322. The first end 321 of the elongated member is coupled to the inner surface 319 of the cap 318. The holder 312 is coupled to the second end 322 of the elongated member 319. A piece of filter paper 323 is of predetermined dimensions and is mechanically coupled to the holder 312 so that a technician can collect a sample of saliva without touching the sample. The sample adequacy system 314 includes a plastic lens 324 and a hole 325 in the top surface of the holder 312 into which the plastic lens 324 is disposed. The top portion 326 of the piece of filter paper 323 is treated with a chemical reagent 327 which reacts with saliva by changing its color from a first color to a second color.

Referring to FIG. 13 in conjunction with FIG. 14, FIG. 15, FIG. 16 and FIG. 17 before the saliva collector 313 has been placed in a subject's mouth the top portion 326 of the piece of filter paper 323 is of the color blue. When an adequate amount of saliva has been collected the saliva in the piece of filter paper 323 will reach the chemical reagent 327, and change the color blue to clear. Each sample of saliva will be collected wet and during the initial stages of testing of the saliva sampling device 310 a corresponding sample of blood serum is being compared thereto. Once an adequate amount of saliva has been collected the saliva the holder 312 and the piece of filter paper 320 are placed into the sample container 311 and shaken vigorously enough to separate the piece of filter paper 323 from the holder 312.

Figure 18:
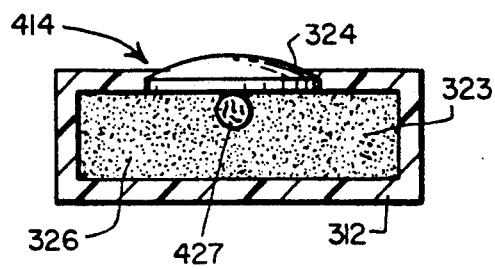
FIG. 18 is a cross-sectional view of a saliva collector of a saliva sampling device which includes a sample adequacy system in accordance with the principles of the fifth embodiment showing the sample adequacy system before the saliva collector has been placed in a subject's mouth.
Figure 19:
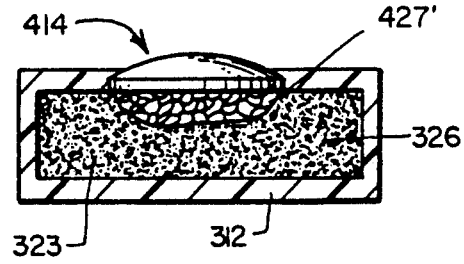
FIG. 19 is a cross-sectional view of the saliva collector of FIG. 18 showing the sample adequacy system after the saliva collector has collected an adequate sample of saliva.

Referring to FIG. 13 in conjunction with FIG. 14, FIG. 18 and FIG. 19 a sample adequacy system 414 includes the plastic lens 324 and the hole 325 in the top surface of the holder 312 into which the plastic lens 324 is disposed. The top portion 326 of the piece of filter paper 323 has a compressed sponge 427 which expands which it comes in contact with saliva. When an adequate amount of saliva has been collected the saliva in the piece of filter paper 323 will reach the compressed sponge 427' and expand it.

Figure 20:
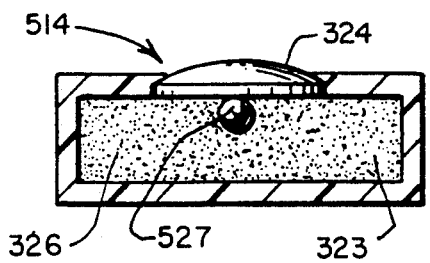
FIG. 20 is a cross-sectional view of a saliva collector of a saliva sampling device which includes a sample adequacy system in accordance with the principles of the sixth embodiment showing the sample adequacy system before the saliva collector has been placed in a subject's mouth.
Figure 21:
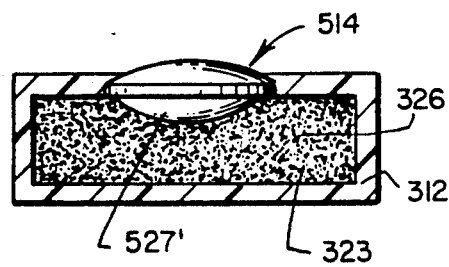
FIG. 21 is a cross-sectional view of the saliva collector of FIG. 20 showing the sample adequacy system after the saliva collector has collected an adequate sample of saliva.
Figure 17:
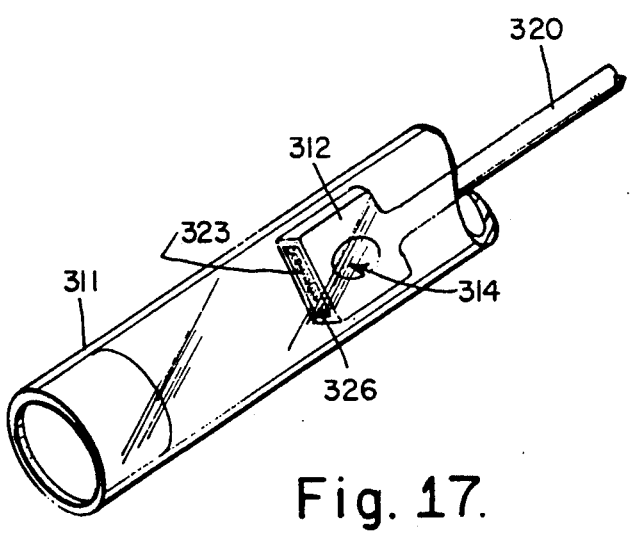
FIG. 17 is a partial perspective view of the saliva sampling device of FIG. 13 in which the piece of filter paper has separated from the saliva collector.

Referring to FIG. 13 in conjunction with FIG. 14, FIG. 20 and FIG. 21 a sample adequacy system 514 includes the plastic lens 324 and the hole 325 in the top surface of the holder 312 into which the plastic lens 324 is disposed. The top portion 326 of the piece of filter paper 323 has an expandable polymeric bead 527 which expands which it comes in contact with saliva. When an adequate amount of saliva has been collected the saliva in the piece of filter paper 323 will reach the expandable polymeric bead 527' and expand it.

Figure 22:
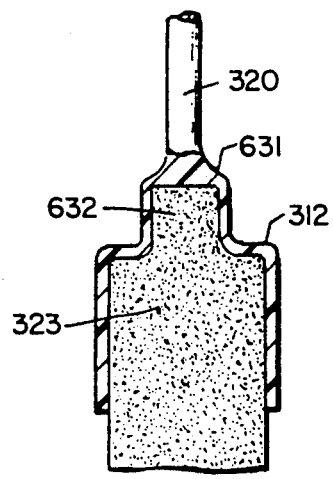
FIG. 22 is a side elevational view in cross-section of a saliva collector of a saliva sampling device in accordance with the principles of the seventh embodiment.

Referring to FIG. 22 the holder 311 has a tab 631 on its top surface adjacent to the second end 322 of the elongated member 320. The corresponding top portion 632 of the piece of filter paper 323 may either be treated with the chemical reagent 327 or have either the compressed sponge 427 or the expandable polymeric bead 527 disposed therein.

Referring to FIG. 23 in conjunction with FIG. 24, FIG. 25 and FIG. 26 a separating device 640 includes a hollow piston 641, which has a first open end 642 and a second open end 643, and a cylindrical, rubber gasket 644 which is snugly disposed in the second end 643. The cylindrical, rubber gasket 644 is slidably coupled to the sample container 311 of the saliva sampling device 310. The cylindrical, rubber gasket 644 has a flange 645 and an opening 646 into which a filter 647 is placed for use in separating the measured sample of saliva from the piece of filter paper 323. The hollow piston 640 is used to press the saliva from the sample container 311 into the hollow piston 641.

U.S. Pat. No. 4,895,808 teaches a test tube and tube-like adsorption column. The sample to be analyzed is prepared in solution and placed in the test tube. The tube-like adsorption column which has a seal and a valve member is forcefully fed into the test tube to force solutions through the valve member into the column and through a filter.

Figure 27:
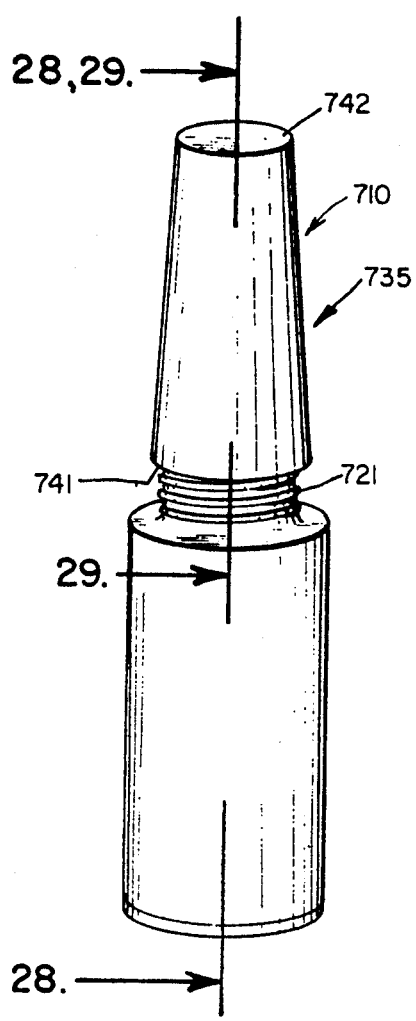
FIG. 27 is a perspective view of a saliva sampling device which is used for collecting a measured sample of saliva in accordance with the principles of the eighth embodiment.
Figure 28:
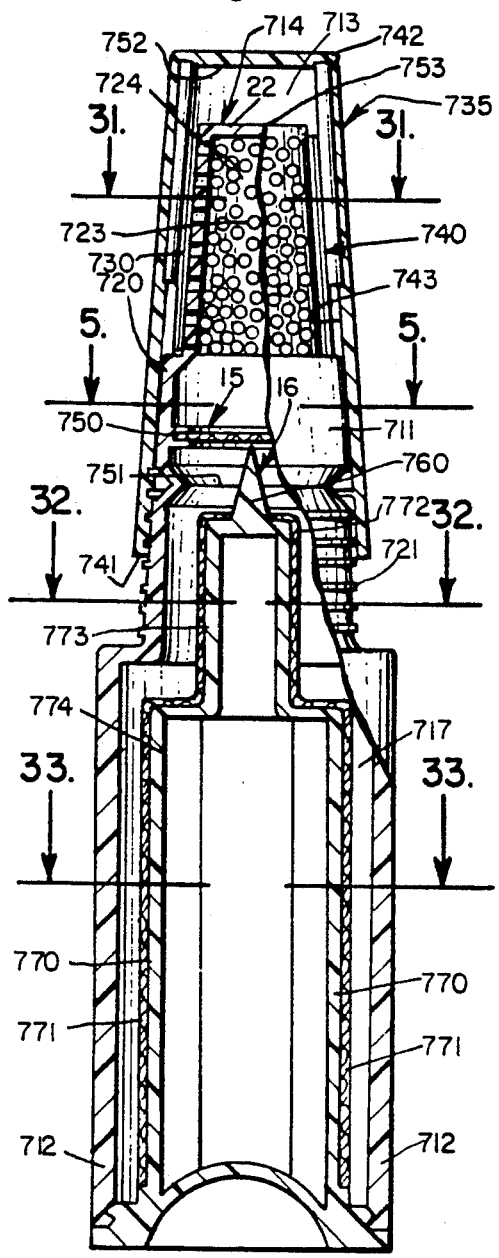
FIG. 28 is a longitudinal view in cross-section of the saliva sampling device of FIG. 27.
Figure 29:
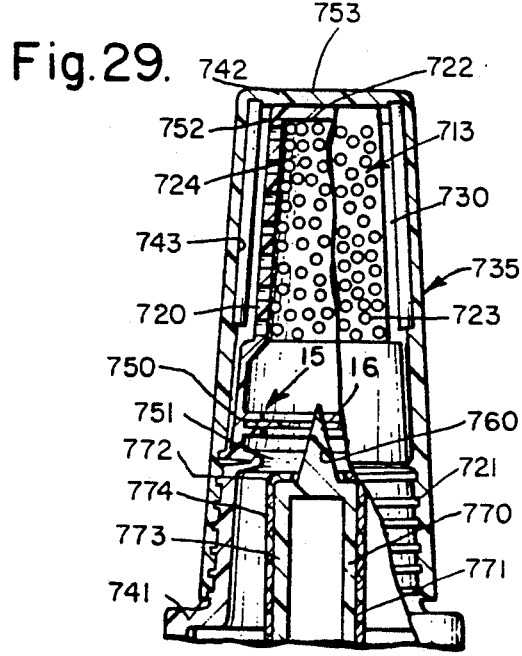
FIG. 29 is a partial longitudinal view in cross-section of the saliva sampling device of FIG. 27.
Figure 30:
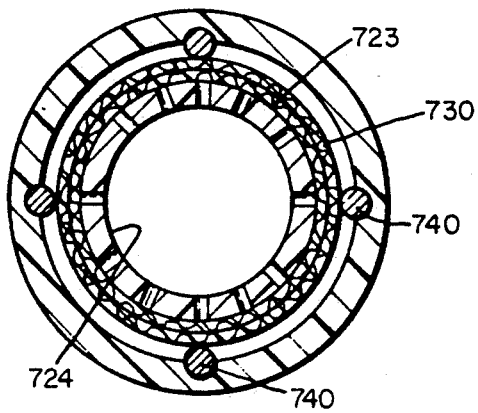
FIG. 30 is a transverse view in cross-section of the saliva sampling device of FIG. 27 taken along line 30—30 of FIG. 28.
Figure 31:
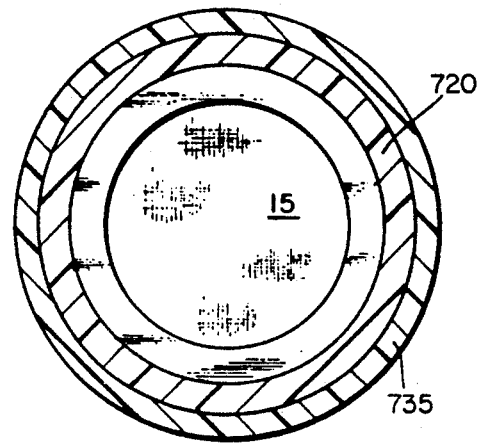
FIG. 31 is a transverse view in cross-section of the saliva sampling device of FIG. 27 taken along line 31—31 of FIG. 28.
Figure 32:
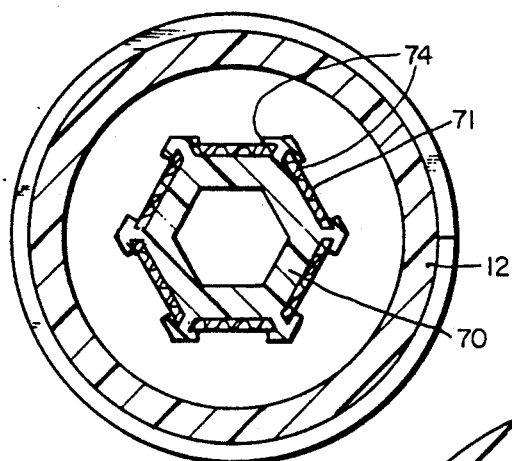
FIG. 32 is a transverse view in cross-section of the saliva sampling device of FIG. 27 taken along line 32—32 of FIG. 28.
Figure 33:
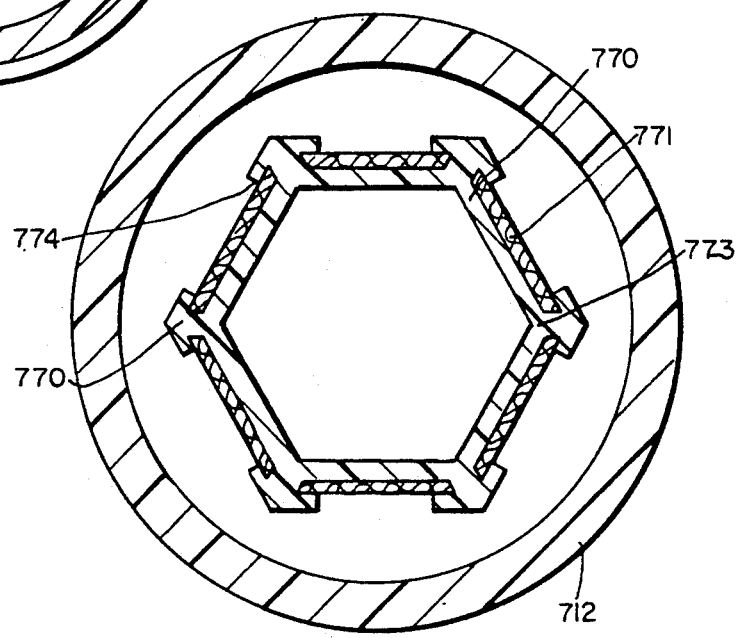
FIG. 33 is a transverse view in cross-section of the saliva sampling device of FIG. 27 taken along line 33—33 of FIG. 28.

Referring to FIG. 27 in conjunction with FIG. 28 a saliva sampling device 710 includes a sample container which has a first portion 711 and a second portion 712, a saliva collector 713, a removing mechanism 714, a sealing mechanism 715, a opening mechanism 716 and a testing mechanism 717. The saliva collector 713 collects a measured sample of saliva and is coupled to the sample container in the first portion 711 thereof. The first removing mechanism 714 removes the measured sample of the saliva from the saliva collector 713 and is coupled to the sample container in the first portion 711 thereof. The sealing mechanism 715 seals the first portion 711 of the sample container from the second portion 712. The opening mechanism 716 opens the sealing mechanism 715 so that the measured sample of the saliva may enter the second portion 712 of the sample container from the first portion 711 thereof. The first testing mechanism 717 tests the measured sample of the saliva and is coupled to the sample container in the second portion 712 thereof.

Still referring to FIG. 27 in conjunction with FIG. 28, FIG. 29, FIG. 30, FIG. 31, FIG. 32 and FIG. 33 the first portion 711 of the sample container is a hollow, truncated cone 720 which has an open threaded end 721, a closed end 722, a holey outer surface 723 and an inner surface 724. The saliva collector 713 includes a piece 730 of filter paper which is of predetermined dimensions. The piece 730 of filter paper is mechanically coupled to the hollow, truncated cone 720 and is disposed on the holey outer surface thereof 723. The removing mechanism 714 includes a cap 735 and a pressing mechanism 740. The cap 735 has a threaded open end 741, a closed end 742 and an inner surface 743. The threaded open end 741 of the cap 735 is adapted to be threadedly coupled to the threaded, open end 721 of the hollow, truncated cone 720 so that the piece 730 of filter paper is disposed between the inner surface 743 of the cap 735 and the holey outer surface 723 of the hollow, truncated cone 720. The pressing mechanism 740 presses the piece 730 of filter paper and is disposed between the inner surface 743 of the cap 735 and the holey outer surface 723 of the hollow, truncated cone 720 and is mechanically coupled to the piece 730 of filter paper. The sealing mechanism 715 is a membrane 750 which is disposed adjacent to the open, threaded end 721 of the hollow, truncated cone 720 on the inner surface 724 thereof. The hollow, truncated cone 720 has a collapsible portion 751 so that the inner top 752 of the cap 735 engages the outer top 753 of the hollow, truncated cone 720 as the cap 735 is being threaded downward causing the collapsible portion 751 thereof to collapse to allow the cap 735 to continue to be threaded downward. The opening mechanism 716 includes a breaking mechanism 760 which breaks the membrane 750 when the cap 735 is threaded downward. The testing mechanism 717 includes a first testing pole 770 and a plurality of reagent test strips 771. The testing pole 770 is disposed in the second portion 712 of the sample container and has a first portion 772 which functions as the breaking mechanism 760 and a second portion 773 which forms channels 774 through which the measured amount of the saliva flows. Each reagent test strip 771 is mechanically coupled to the testing pole 770 and contacts a portion of the measured amount of the saliva as it flows in the channels 774.

Figure 34:
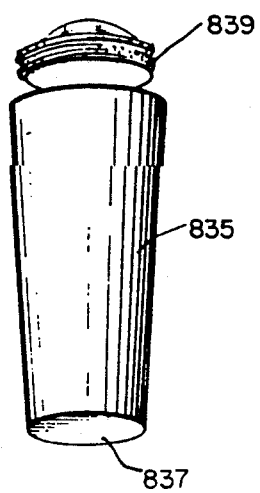
FIG. 34 is a perspective view of a cap and a lid of a saliva sampling device in accordance with the principles of the ninth embodiment.
Figure 35:
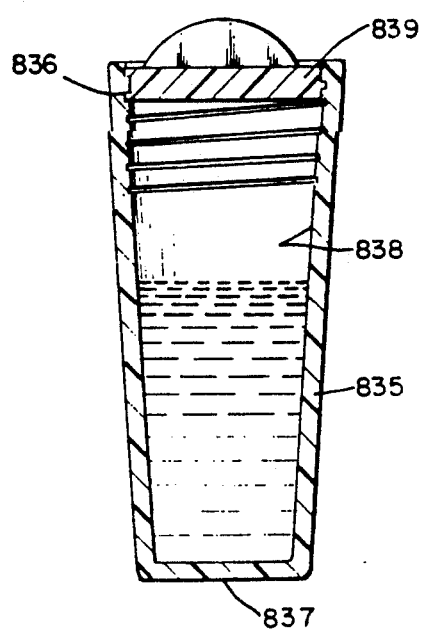
FIG. 35 is a longitudinal view in cross-section of the cap and the lid of FIG. 34 of the saliva sampling device of FIG. 34.
Figure 36:
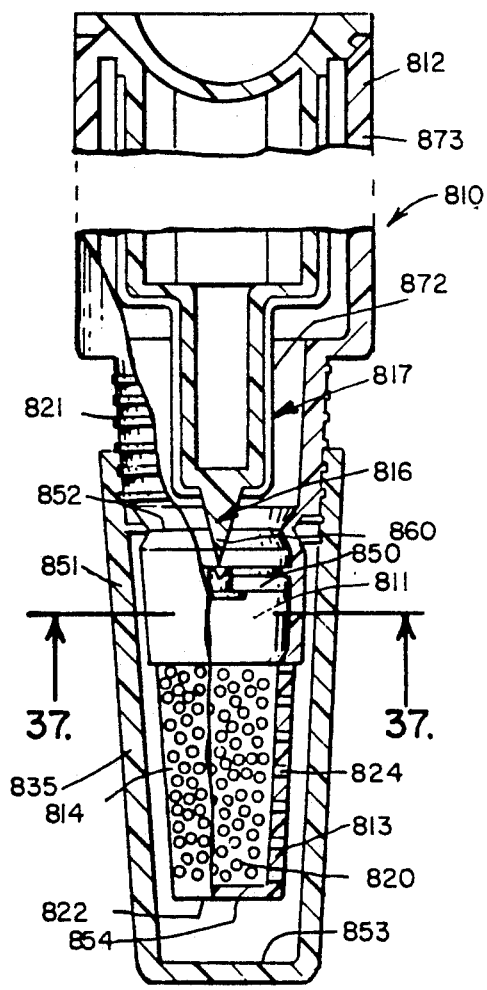
FIG. 36 is a longitudinal view in cross-section of saliva sampling device of FIG. 34.
Figure 37:
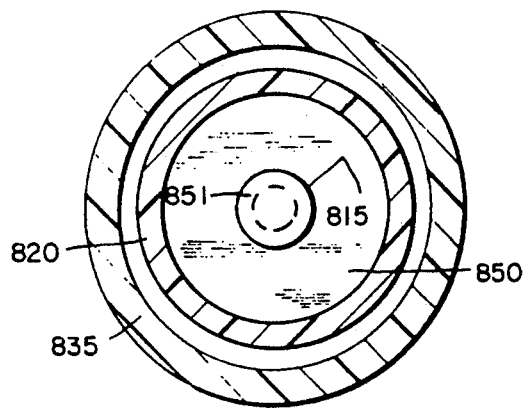
FIG. 37 is a transverse view in cross-section of the saliva sampling device of FIG. 34 taken along line 37—37 of FIG. 36.

Referring to FIG. 34 in conjunction with FIG. 35 and FIG. 36 a saliva sampling device 810 includes a sample container which has a first portion 811 and a second portion 812, a saliva collector 813, a removing mechanism 814, a sealing mechanism 815, a opening mechanism 816 and a testing mechanism 817. The saliva collector 813 collects a measured sample of saliva and is coupled to the sample container in the first portion 811 thereof. The removing mechanism 814 removes the measured sample of the saliva from the saliva collector 813 and is coupled to the sample container in the first portion 811 thereof. The sealing mechanism 815 seals the first portion 811 of the sample container from the second portion 812. The opening mechanism 816 opens the sealing mechanism 815 so that the measured sample of the saliva may enter the second portion 812 of the sample container from the first portion 811 thereof. The testing mechanism 817 tests the measured sample of the saliva and is coupled to the sample container in the second portion 812 thereof.

Still referring to FIG. 34 in conjunction with FIG. 35 and FIG. 36. the first portion 811 of the sample container is a hollow, truncated cone 820 which has an open threaded end 821, a closed end 822, a holey outer surface 823 and an inner surface 824. The saliva collector 813 includes a cap 835 which has a threaded open end 836, a closed end 837 and an inner surface 838. The threaded open end 821 of the cap 820 is adapted to be threadedly coupled to both a threaded lid 839 and the open end 821 of the hollow, truncated cone 820 so that the measured amount of saliva is disposed between the inner surface 838 of the cap 835 and the holey outer surface 823 of the hollow, truncated cone 820. The sealing mechanism 815 is a first flange 850 and a first plug 851. The first flange 850 is disposed adjacent to the open, threaded end 821 of the hollow, truncated cone 820 on the inner surface 824 thereof. The first plug 851 is disposed in the first flange 850 and snugly, but removably coupled thereto. The hollow, truncated cone 820 has a collapsible portion 852 so that the inner top 853 of the cap 835 engages the outer top 854 of the hollow, truncated cone 820 as the cap 835 is being threaded downward causing the collapsible portion 852 thereof to collapse to allow the cap 835 to continue to be threaded downward. The opening mechanism 816 includes a lifting mechanism 860 which lifts the first plug 851 from the first flange 850 when the cap 835 is threaded downward. The testing mechanism 817 includes a second testing pole 870 and a plurality of reagent test strips 871. The testing pole 870 is disposed in the second portion 812 of the sample container and has a first portion 872 which functions as the lifting mechanism 860 and a second portion 873 which forms channels 874 through which the measured amount of the saliva flows. Each reagent test strip 871 is mechanically coupled to the testing pole 870 and contacts a portion of the measured amount of the saliva as it flows in the channels 874.

Referring to FIG. 39 in conjunction with FIG. 40 and FIG. 41 a saliva sampling device 910 includes a sample container which has a first portion 911 and a second portion 912, a saliva collector 913, a removing mechanism 914, a sealing mechanism 915, an opening mechanism 916 and a transporting mechanism 917. The saliva collector 913 collects a measured sample of saliva and is coupled to the sample container in the first portion 911 thereof. The removing mechanism 914 removes the measured sample of the saliva from the saliva collector 913 and is coupled to the sample container in the first portion 911 thereof. The sealing mechanism 915 seals the first portion 911 of the sample container from the second portion 912. The opening mechanism 916 opens the sealing mechanism 915 so that the measured sample of the saliva may enter the second portion 912 of the sample container from the first portion 911 thereof. The transporting mechanism 917 is mechanically coupled to the sample container in the second portion 912 thereof.

Still referring to FIG. 39 in conjunction with FIG. 40 and FIG. 41 the first portion 911 of the sample container is a hollow, truncated cone 920 which has an open threaded end 921, a closed end 922, a holey outer surface 923 and an inner surface 924. The saliva collector 913 includes a piece 930 of filter paper which is of predetermined dimensions. The piece 930 of filter paper is mechanically coupled to the hollow, truncated cone 920 and is disposed on the holey outer surface thereof 923. The removing mechanism 914 includes a cap 935 and a pressing mechanism 940. The cap 935 has a threaded open end 941, a closed end 942 and an inner surface 943. The threaded open end 941 of the cap 935 is adapted to be threadedly coupled to the threaded, open end 921 of the hollow, truncated cone 920 so that the piece 930 of filter paper is disposed between the inner surface 943 of the cap 935 and the holey outer surface 923 of the hollow, truncated cone 920. The pressing mechanism 940 presses the piece 930 of filter paper and is disposed between the inner surface 943 of the cap 935 and the holey outer surface 923 of the hollow, truncated cone 920 and is mechanically coupled to the piece 930 of filter paper. The sealing mechanism 915 is a flange 950 and a plug 951. The flange 950 is disposed adjacent to the open, threaded end 921 of the hollow, truncated cone 920 on the inner surface 924 thereof. The plug 951 is disposed in the flange 950 and snugly, but removably coupled thereto. The hollow, truncated cone 920 has a collapsible portion 952 so that the inner top 953 of the cap 935 engages the outer top 954 of the hollow, truncated cone 920 as the cap 935 is being threaded downward causing the collapsible portion 952 thereof to collapse to allow the cap 935 to continue to be threaded downward. The opening mechanism 916 includes a lifting mechanism 960 which is a lifting collar 961 with a flange 962 and which lifts the plug 951 from the flange 950 when the cap 935 is threaded downward. The transporting mechanism 918 is a sample container 980 with a threaded, open end 981 and a closed end 982. The second portion 912 is a collar 990 with a threaded inner surface. The sample container 980 is threadedly coupled to the collar 990 with the lifting collar inserted into the collar 980.

Figure 42:
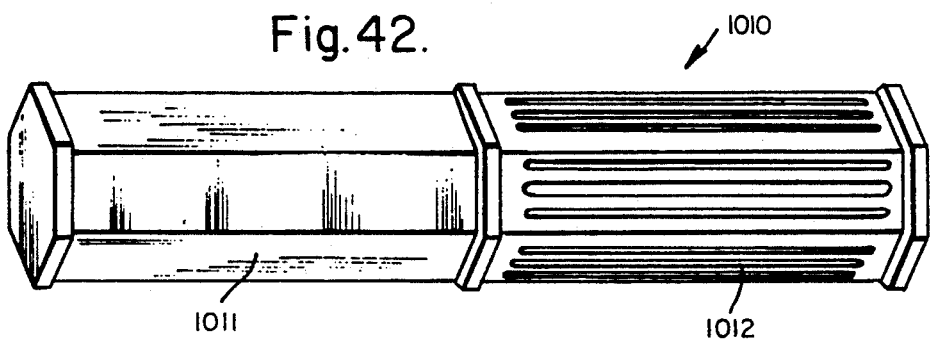
FIG. 42 is a perspective view of a saliva sampling device in accordance with the principles of the eleventh embodiment.
Figure 43:
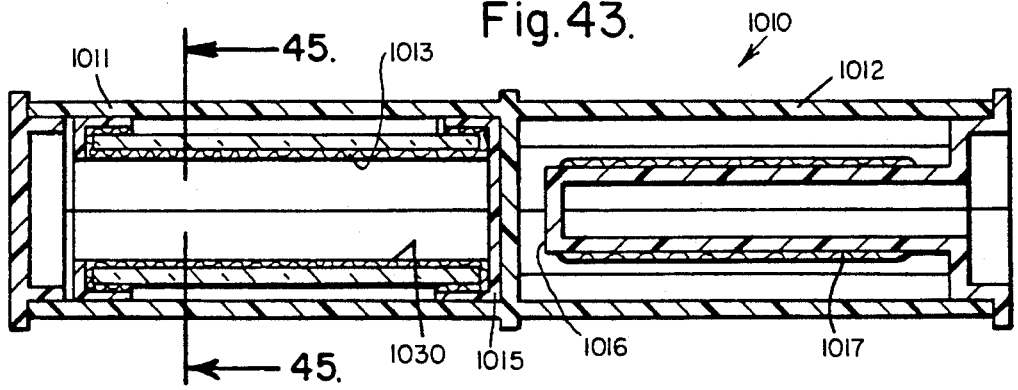
FIG. 43 is a first longitudinal view in cross-section of the saliva sampling device of FIG. 42.
Figure 44:
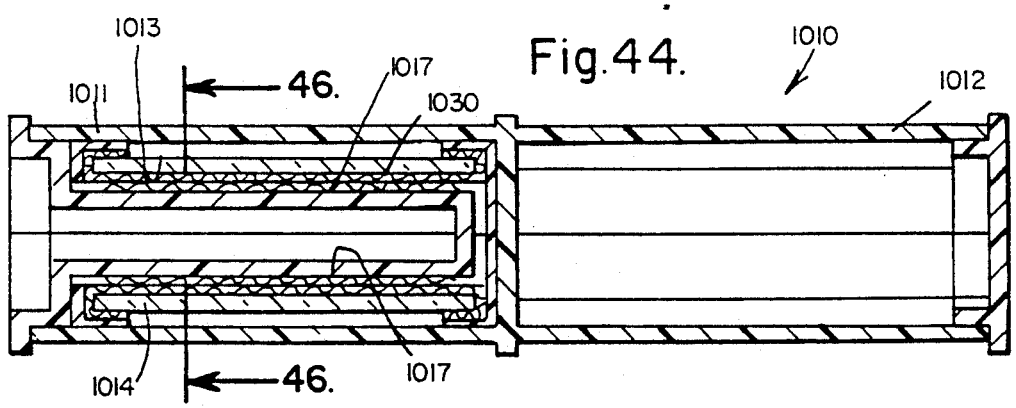
FIG. 44 is a second longitudinal view in cross-section of the saliva sampling device of FIG. 42.

Referring to FIG. 42 in conjunction with FIG. 43 and FIG. 44 a saliva sampling device 1010 includes a sample container which has a first portion 1011 and a second portion 1012, a saliva collector 1013, a removing mechanism 1014, a sealing mechanism 1015, an opening mechanism 1016 and a testing mechanism 1017. The saliva collector 1013 collects a measured sample of saliva and is coupled to the sample container in the first portion 1011 thereof. The removing mechanism 1014 removes the measured sample of the saliva from the saliva collector 1013 and is coupled to the sample container in the first portion 1011 thereof. The sealing mechanism 1015 seals the first portion 1011 of the sample container from the second portion 1012. The opening mechanism 1016 opens the sealing mechanism 1015 so that the measured sample of the saliva may enter the second portion 1012 of the sample container from the first portion 1011 thereof. The testing mechanism 1018 tests the measured sample of the saliva and is coupled to the sample container in the second portion 1012 thereof.

Figure 45:
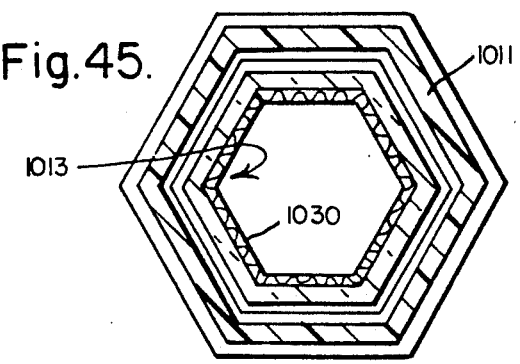
FIG. 45 is a transverse view in cross-section of the saliva sampling device of FIG. 42 taken along line 45—45 of FIG. 43.
Figure 46:
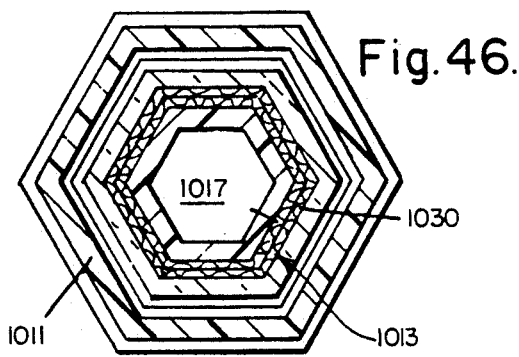
FIG. 46 is a transverse view in cross-section of the saliva sampling device of FIG. 42 taken along line 46—46 of FIG. 44.

Still referring to FIG. 43 in conjunction with FIG. 44, FIG. 45 and FIG. 46 the first portion 1011 of the sample container has a saliva collector 1013 Which includes a piece 1030 of filter paper which is of predetermined dimensions. The piece 1030 of filter paper is mechanically is disposed on the removing mechanism 1014.

Referring to FIG. 47 in conjunction with FIG. 48 and FIG. 49 a saliva sampling device 1110 includes a sample container 1111 having a cap 1112, a saliva collector 1113, a collection container 1114 and a sample adequacy system 1115. The sample container 1111 has an open end 1116 and a closed end 1117. The sample container 1111 has a breakable seal 1118 is disposed at the closed end 1117. The collection container 1114 has an open end 1119, which the cap 1112 is adapted to close, and a closed end 1120. The cap 1112 seals the sample container 1111 air-tight. The collection container 1114 has a seal-breaking member 1121 disposed at the closed end thereof. The saliva collector 1113 includes a holder 1122, an elongated member 1123 and a piece of filter paper 1124. The elongated member 1123 has a first end 1125 and a second end 1126. The first end 1125 of the elongated member 1124 is coupled to a push tab 1127. The holder 1122 is coupled to the second end 1126 of the elongated member 1123. The piece of filter paper 1124 is of predetermined dimensions and is mechanically coupled to the holder 1122 so that a technician can collect a sample of saliva without touching the sample. The saliva collector 1113 selectively receives a sample of saliva.

Referring to FIG. 48 in conjunction with FIG. 50, FIG. 51 and FIG. 52 the sample adequacy system 1115 includes a plastic lens 1129 and a hole 1130 in the top surface of the holder 1122 into which the plastic lens 1129 is disposed. The top portion 1131 of the piece of filter paper 1124 is treated with a chemical reagent 1132 which reacts with saliva by changing its color from a first color, e.g. blue, to a second color, e.g. clear. Before the saliva collector 1113 has been placed in a subject's mouth the top portion 1131 of the piece of filter paper 1124 is of the color blue. When an adequate amount of saliva has been collected the saliva in the piece of filter paper 1124 will reach the chemical reagent 1132' and change the color blue to clear. In other embodiments the sample adequacy system 1115 includes either a compressed sponge or an expandable polymeric beam which expands which it comes in contact with saliva and which is disposed in the top portion 1131 of the piece of filter paper 1124. When the saliva collector 1113 has collected an adequate sample, the saliva will reach either the compressed sponge or the expandable polymeric bead and expand it.

Referring to FIG. 47 in conjunction with FIG. 48, FIG. 53 and FIG. 56 a buffering solution 1128 is contained in the sample container 1111. In another embodiment the sample container 1111 may be formed out of a non-opaque plastic material. The sample adequacy system 1115 may then include a label having a bottom edge attached to the sample container 1111. The bottom edge of the label is disposed adjacent to the liquid level of the buffering solution 1128. When the saliva collector 1113 is placed in the sample container 1111, if the liquid level of the buffering solution 1128 does not drop below the bottom edge of the label then the collected sample of saliva is of an adequate amount.

Referring to FIG. 47 in conjunction with FIG. 53, FIG. 54, FIG. 55, FIG. 56 and FIG. 57 the sample container 1111 also includes a retaining ridge 1133 and a filtering system 1134 including a rubber o-ring 1135 and a piece of filtering material 1136. The filtering system 1134 is disposed adjacent to the breakable seal 1118. Once an adequate amount of saliva has been collected the saliva the saliva collector 1113 is inserted into the sample container 1111, after the cap 1112 has been removed therefrom, in order to mix the buffering solution 1128 and the sample of saliva together. When the sample container 1111 is inserted into the collection container 1114 and pressed downward the seal-breaking member 1121 breaks the breakable seal 1118 and the mixture of the buffering solution 1128 and the sample of saliva flows into the collection container 1114 through the filtering system 1134. The retaining ridge 1133 keeps the saliva collector 1113 from being removed from the sample container 1111 in order to prevent the saliva collector 1113 from being used more than once. The collection container 1114 has the mixture of the buffering solution 1128 and the saliva contained therein and is sealed by the cap 1112.

Figure 58:
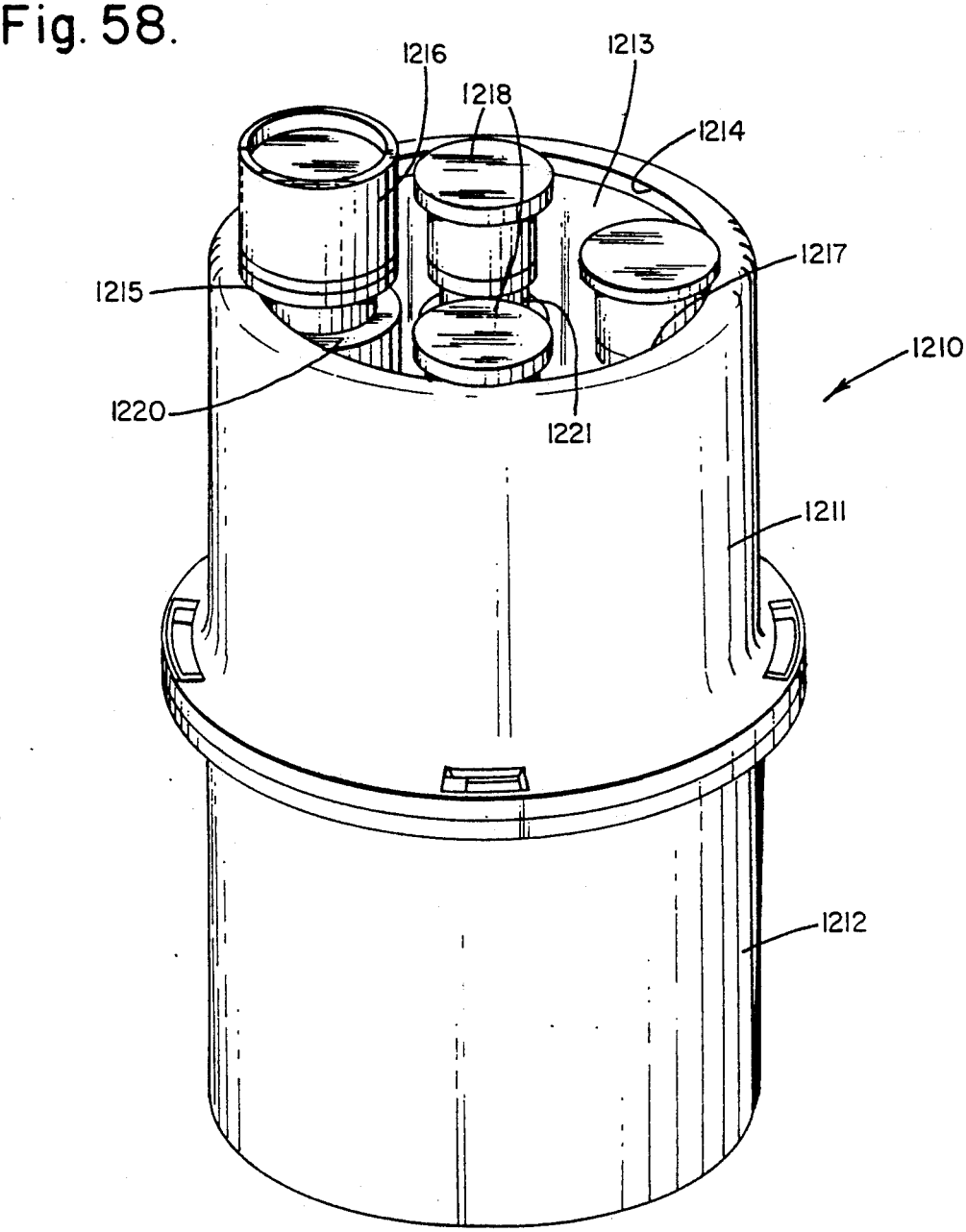
FIG. 58 is a perspective view of a saliva sampling device in accordance with the principles of the thirteenth embodiment.

Referring to FIG. 58 a saliva sampling device 1210 includes a first hollow, cylindrical member 1211, a second hollow, cylindrical member 1212 and a rotatable cylinder 1213. The first hollow, cylindrical member 1211 has a innerly overhanging peripheral circular rim 1214. The first hollow, cylindrical member 1211 is coupled to the second hollow, cylindrical member 1212. The saliva sampling device 1210 also includes a sample container 1215, which has a cap 1216, three reagent containers 1217, each of which has a cap 1218 and a saliva collector 1219. The rotatable cylinder 1213 has a first bore 1220 and three second bores 1221. The rotatable cylinder 1213 is disposed in and rotatively coupled to the first hollow, cylindrical member 1211. The sample container 1215 is disposed in and slidably coupled to the first bore 1220. Each of the three reagent containers 1217 is disposed in and slidably coupled to one the three second bores 1221.

Figure 59:
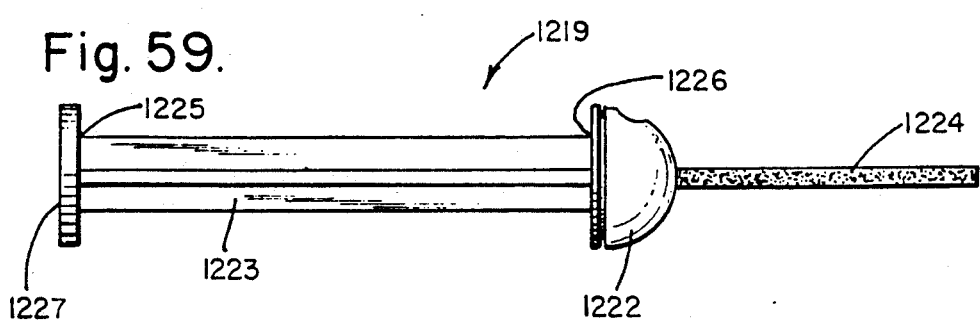
FIG. 59 is an elevational view of a saliva collector of the saliva sampling device of FIG. 58 which includes a holder, an elongated member, a piece of filter paper and a sample adequacy system.

Referring to FIG. 58 in conjunction with FIG. 59, FIG. 60 and FIG. 61 the saliva collector 1219 includes a holder 1222, an elongated member 1223 and a piece of filter paper 1224. The elongated member 1223 has a first end 1225 and a second end 1226. The first end 1225 of the elongated member 1223 is coupled to a push tab 1227. The holder 1222 is coupled to the second end 1226 of the elongated member 1223. The piece of filter paper 1224 is of predetermined dimensions and is mechanically coupled to the holder 1222 so that a technician can collect a sample of saliva without touching the sample. The saliva collector 1219 selectively receives a sample of saliva. The sample container 1215 has an open end 1228 and a closed end 1229 with a breakable seal 1230 which is disposed at the closed end 1229. The sample container 1215 contains a buffering solution 1231. The saliva collector 1219 is adapted to be inserted into the sample container 1215. The sample container 1215 also includes a retaining ridge 1232 and a filtering system 1233 including a rubber o-ring 1234 and a piece of filtering material 1235. The filtering system 1233 is disposed adjacent to the breakable seal 1230. Once an adequate amount of saliva has been collected the saliva the saliva collector 1219 is inserted into the sample container 1215, after the cap 1216 has been removed therefrom, in order to mix the buffering solution 1231 and the sample of saliva together.

Referring to FIG. 58 in conjunction with FIG. 62 and FIG. 63 each reagent container 1217 has an open end 1236, which is closed by the cap 1218 and a closed end 1237 with a breakable seal 1238 which is disposed at the closed end 1237. Each reagent container 1215 contains a preselected reagent solution 1239. The innerly overhanging peripheral circular rim 1214 has with a curved notch 1240 therein.

Referring to FIG. 63 in conjunction with FIG. 64 the second hollow, cylindrical member 1212 has a top flat member 1241 which has a drain 1242 with a seal-breaking member disposed 1243 therein and a collection container 1244. When the curved notch 1240 is not aligned with the first bore 1220 the saliva collector 1219 can not press the sample container 1215 downward.

Referring to FIG. 65 in conjunction with FIG. 66 and FIG. 67 when the curved notch 1240 is aligned with the first bore 1220 the saliva collector 1219 presses the sample container 1215 downward s that the seal-breaking member 1243 breaks the breakable seal 1230 in order for the mixture of the buffering solution 1230 and the sample of saliva to flow into the drain 1242 in the top flat member 1241. When the sample container 1215, which is inserted into the first bore 1220, is pressed downward the seal-breaking member 1243 breaks the breakable seal 1230 and the mixture of the buffering solution 1231 and the sample of saliva flows into the collection container 1244 through the filtering system 1233. The retaining ridge 1232 keeps the saliva collector 1219 from being removed from the sample container 1215 in order to prevent the saliva collector 1219 from being used more than once. The collection container 1244 has the mixture of the buffering solution 1231 and the saliva contained therein.

Referring to FIG. 66 in conjunction with FIG. 68 the collection container 1244 includes an inlet 1245, and a testing pole 1246 with reagent test strips 1247 disposed thereon. The second hollow, cylindrical member 1212 is formed from a non-opaque plastic material Referring to FIG. 67 in conjunction with FIG. 58 and FIG. 69 a locking mechanism 1248 locks the first hollow, cylindrical member 1211 to the second hollow, cylindrical member 1212.

Referring to FIG. 70 inconjunction with FIG. 71 and FIG. 72 when the curved notch 1240 is selectively aligned with one of the three second bores 1221 one of the reagent containers 1217 is selectively pressed downward so that the seal-breaking member 1243 breaks the breakable seal 1238 thereof in order for the pre-selected reagent solution 1239 to flow into the drain 1242 in the top flat member 1241 and mix together with the mixture of the buffering solution and the sample of saliva in the collection container 1247.

Referring to FIG. 73 a saliva sampling device 1310 includes a first hollow, cylindrical member 1311, a second hollow, cylindrical member 1312 and a cylinder 1313. The first hollow, cylindrical member 1311 has a innerly overhanging peripheral circular rim 1314. The first hollow, cylindrical member 1311 is coupled to the second hollow, cylindrical member 1312. The saliva sampling device 1310 also includes a five sample containers 1315 each of which has a cap 1316. The cylinder 1313 has a five bores 1317. The cylinder 1313 is disposed in and coupled to the first hollow, cylindrical member 1311. Each sample container 1315 has a cap 1316 and is disposed in and slidably coupled to one of the five bores 1318.

Referring to FIG. 74 in conjunction with FIG. 73 the saliva sampling device 1310 further includes five saliva collectors 1319. Each saliva collector 1319 has a holder 1320, an elongated member 1321 and a piece of filter paper 1322. The elongated member 1321 has a first end 1323 and a second end 1324. The first end 1323 of the elongated member 1321 is coupled to a push tab 1324. The holder 1320 is coupled to the second end 1324 of the elongated member 1321. The piece of filter paper 1322 is of predetermined dimensions and is mechanically coupled to the holder 1320 so that a technician can collect a sample of saliva without touching the sample. Each saliva collector 1319 selectively receives a sample of saliva. The sample container 1315 has an open end 1325 and a closed end 1326 with a breakable seal 1327 which is disposed at the closed end 1326. Each sample container 1315 contains a buffering solution 1328. The sample container 1315 also includes a retaining ridge 1329 and a filtering system 1330 including a rubber o-ring 1331 and a piece of filtering material 1332. The filtering system 1330 is disposed adjacent to the breakable seal 1327. Once an adequate amount of saliva has been collected the saliva in each saliva collector 1318 is inserted into one of the sample containers 1315, after the cap 1316 has been removed therefrom, in order to mix the buffering solution 1328 and the sample of saliva together.

Referring to FIG. 75 in conjunction with FIG. 76, FIG. 77 and FIG. 78 the second hollow, cylindrical member 1312 has a top flat member 1333 which has five drains 1334. Each drain 1334 has a seal-breaking member 1335 disposed therein and a collection container 1336. Once each of the five saliva collectors 1319 has collected an adequate sample of saliva it is inserted into one of the five sample containers 1315 so that the buffering solution 1328 and each of five different samples of saliva from five different people are mixed together in each of the five sample containers 1315. Each sample container 1315 is inserted into one of the five bores in the cylinder 1313. Each saliva collector 1319 presses the sample container 1315 downward so that each seal-breaking member 1335 breaks one of the five breakable seals 1327 so that each mixture of the buffering solution 1328 and each sample of saliva flow into the collection container 1336 through the filtering system 1330. The retaining ridge 1329 keeps the saliva collector 1319 from being removed from the sample container 1315 in order to prevent the saliva collector 1319 from being used more than once.

Referring to FIG. 79 in conjunction with FIG. 80 and FIG. 81 a saliva sampling device 1410 includes a housing 1411 and a saliva collector 1412 which may be inserted into the housing 1411. The saliva collector 1412 includes a holder 1413, an elongated member 1414 and a piece of filter paper 1415.

Referring to FIG. 82 in conjunction with FIG. 79 and FIG. 83 the saliva sampling device 1410 also includes a testing mechanism 1416 which has reagent strip 1417 attached thereto. The testing mechanism 1416 is coupled to the housing 1411.

Referring to FIG. 84 in conjunction with FIG. 79, FIG. 85 and FIG. 86 the saliva sampling device 1410 further includes a collection container 1418 and a cap 1419. In another embodiment the collection container 1418, once the cap 1419 has been removed, is coupled to the housing 1411.

Referring to FIG. 87 in conjunction with FIG. 88 a saliva sampling device 1510 includes includes a sample container 1511 having a cap 1512, a saliva collector 1513 and a collection container 1514. The sample container 1511 has an open end 1515 and a closed end 1516. The sample container 1511 has a breakable seal 1517 is disposed at the closed end 1516. The collection container 1514 has an open end 1518, which the cap 1512 is adapted to close, and a closed end 1519. The cap 1512 seals the sample container 1511 air-tight. The collection container 1514 has a seal-breaking member 1521 disposed at the closed end thereof. The saliva collector 1513 includes a holder 1521, an elongated member 1522 and a piece of filter paper 1523. The elongated member 1522 has a first end 1524 and a second end 1525. The first end 1524 of the elongated member 1523 is coupled to a push tab 1526. The holder 1521 is coupled to the second end 1525 of the elongated member 1522. The piece of filter paper 1523 is mechanically coupled to the holder 1521. The collection container 1514 includes an automatic testing mechanism 1526. The sample container 1511 also includes a retaining ridge 1527 and a filtering system 1528 including a rubber o-ring 1529 and a piece of filtering material 1530. The filtering system 1528 is disposed adjacent to the breakable seal 1517. Once an adequate amount of saliva has been collected the saliva the saliva collector 1513 is inserted into the sample container 1511, after the cap 1512 has been removed therefrom, in order to mix a buffering solution 1531 and the sample of saliva together. When the sample container 1511 is inserted into the collection container 1514 and pressed downward the seal-breaking member 1521 breaks the breakable seal 1517 and the mixture of the buffering solution 1531 and the sample of saliva flows into the automatic testing mechanism 1526 through the filtering system 1528. The retaining ridge 1529 keeps the saliva collector 1513 from being removed from the sample container 1511 in order to prevent the saliva collector 1513 from being used more than once.

Referring to FIG. 87 in conjunction with FIG. 89 the automatic testing mechanism 1526 includes a rotatable hollow shaft 1532, a rotatable non-opaque base plate 1533, a rotatable test disc 1534, a cover plate 1535, a rotatable plate 1536 with a fluid coupler 1537 and a cylinder 1538 with a plurality of inverted bores 1538. The hollow shaft 1532 is fixedly coupled to the rotatable non-opaque base plate 1533, the rotatable test disc 1534 and the rotatable plate 1536 with a fluid coupler 1537. The cover plate 1535 and the cylinder 1538 are coupled non-rotatively to the collection container 1514.

Referring to FIG. 90 another automatic testing mechanism 1626 includes a rotatable hollow shaft 1632, a rotatable non-opaque base plate 1633, a rotatable test disc 1634, a cover plate 1635, a rotatable plate 1636 with a plurality of fluid couplers 1637 and a cylinder 1638 with a plurality of inverted bores 1638. The hollow shaft 1632 is fixedly coupled to the rotatable non-opaque base plate 1633, the rotatable test disc 1634 and the rotatable plate 1636 with a fluid coupler 1637. The cover plate 1635 and the cylinder 1638 are coupled non-rotatively to the collection container 1614.

From the foregoing it can be seen that saliva sampling devices have been described. It should be noted that the sketches are not drawn to scale and that distance of and between the figures are not to be considered significant.

Accordingly it is intended that the foregoing disclosure and showing made in the drawing shall be considered only as an illustration of the principle of the present invention.

What is claimed is:

1. A saliva sampling device comprising:
   a. a collection container having a first opening;
   b. a sample container having an inner wall surface, a second opening, a first end spaced from said second opening and a passageway through said first end, said first end being sized to fit within said first opening of said collection container;
   c. a selective closure in said passageway;
   d. a saliva collector sized to fit through said second opening, said saliva collector including a piston closely fitting within said inner wall surface of said sample container to seal therebetween, a piece of filter paper being fixed to said piston and a rigid handle extending to said passageawy so that when said saliva collector is inserted into said sample container to a sample removal position said piece of filter paper is squeezed at said passageway; and
   e. a retaining ridge disposed on said inner wall surface whereby said retaining ridge secures said piston within said sample container at said sample removal position.

2. A saliva sampling device according to claim 1 said saliva collector includes
   an indicator activated by a preselected amount of the received sample of saliva and disposed in said piston of said sample collector and apart from said piece of filter paper so that said indicator does not interfere with the collection of a sample of saliva, said indicator being coupled to said piece of filter paper so that when said sample collector is inserted into a test subject's mouth saliva fluidly couples said piece of filter paper to said indicator.

3. A saliva sampling device according to claim 2 said sample container comprises a filtering system including a rubber o-ring and a piece of filtering material, said filtering system disposed adjacent to said selective closure.

4. A saliva sampling device according to claim 2 wherein said indicator comprises a chemical reagent which reacts with saliva by changing the color of said chemical reagent from a first color to a second color and which treats a portion of said piece of filter paper whereby, when said saliva collector has collected an adequate amount, the saliva will reach said chemical reagent and change the color of said chemical reagent from said first color to said second color.

5. A saliva sampling device according to claim 4 wherein said piston has a hole and said indicator further comprises a plastic lens which is disposed in said hole of said piston over said chemical reagent.

6. A saliva sampling device according to claim 2 wherein said indicator comprises a compressed sponge which expands which it comes in contact with saliva and which is disposed in a portion of said piece of filter paper whereby, when said saliva sampling device has collected an adequate sample, the saliva will reach said compressed sponge and expand it.

7. A saliva sampling device according to claim 5, said piston has a hole and said indicator further comprises a plastic lens which is disposed in said hole of said piston over said compressed sponge.

8. A saliva sampling device according to claim 2 wherein said indicator comprises an expandable polymeric bead which expands which it comes in contact with saliva and which is disposed in a portion of said piece of filter paper whereby, when said saliva sampling device has collected an adequate sample, the saliva will reach said polymeric bead and expand it.

9. A saliva sampling device according to claim 8, said piston has a hole and said indicator further comprises a plastic lens which is disposed in said hole of said piston over said polymeric bead.

10. A saliva sampling device comprising:
 a. a collection container having a first opening;
 b. a sample container having a second opening, a first end spaced from said second opening and a passageway through said first end of said sample container, said first end of said sample container being sized to fit within said first opening of said collection container;
 c. a closure element blocking said passageway;
 d. an actuator element extending from one of said closure element and said collection container to contact and interfere with the other of said closure element and said collection container upon insertion of said sample container in said collection container to displace said closure element and open said passageway; and
 e. a saliva collector sized to fit through said second opening of said sample container, said saliva collector including a porous mass coupled to a rigid handle for squeezing said porous mass at said passageway when said porous mass is inserted into said sample container.

11. A saliva sampling device according to claim 10 wherein said actuator element extends from said closure element outwardly of said sample container.

* * * * *